United States Patent
Block et al.

(10) Patent No.: US 12,064,224 B2
(45) Date of Patent: Aug. 20, 2024

(54) CONCENTRIC ARCHITECTURE FOR OPTICAL SENSING

(71) Applicant: Apple Inc., Cupertino, CA (US)

(72) Inventors: Ueyn L. Block, Menlo Park, CA (US); Guocheng Shao, San Jose, CA (US); Itaru L. Hiromi, Cupertino, CA (US); Mathieu Charbonneau-LeFort, San Jose, CA (US); Tobias J. Harrison-Noonan, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 48 days.

(21) Appl. No.: 17/675,399

(22) Filed: Feb. 18, 2022

(65) Prior Publication Data

US 2022/0167864 A1 Jun. 2, 2022

Related U.S. Application Data

(63) Continuation of application No. 16/126,970, filed on Sep. 10, 2018, now Pat. No. 11,266,320.
(Continued)

(51) Int. Cl.
*A61B 5/024* (2006.01)
*A61B 5/00* (2006.01)
(Continued)

(52) U.S. Cl.
CPC ...... *A61B 5/02433* (2013.01); *A61B 5/02438* (2013.01); *A61B 5/0261* (2013.01);
(Continued)

(58) Field of Classification Search
None
See application file for complete search history.

(56) References Cited

U.S. PATENT DOCUMENTS 5,246,002 A 9/1993 Prosser
5,273,036 A 12/1993 Kronberg et al.
(Continued)

FOREIGN PATENT DOCUMENTS

CN 100381095 4/2008
CN 101108126 6/2010
(Continued)

OTHER PUBLICATIONS

Shi, V. et al. (Jul. 20, 2009). "Non-contact Reflection Photoplethysmography Towards Effective Human Physiological Monitoring," Journal of Medical and Biomedical Engineering, 30(3), 161-167.
(Continued)

*Primary Examiner* — Yi-Shan Yang
(74) *Attorney, Agent, or Firm* — Brownstein Hyatt Farber Schreck, LLP

(57) ABSTRACT

An electronic device including optical sensing with a concentric architecture and methods for operation thereof is disclosed. The concentric architecture can include light detector(s) arranged in a concentric manner around light emitter(s). In some examples, at least one light emitter can be located in the center of the device, and each light detector can be located the same separation distance from the light emitter. Each light detector can be arranged such that the separation distance from the centrally located light emitter can be greater than the separation distance from another light emitter. Examples of the disclosure further include a selective transparent layer overlaying the light detector(s). The selective transparent layer can include section(s) transparent to a first wavelength range and non-transparent to a second wavelength ranges. In some examples, the selective transparent layer can further include section(s) transparent to the second wavelength range.

20 Claims, 15 Drawing Sheets

Related U.S. Application Data

(60) Provisional application No. 62/563,594, filed on Sep. 26, 2017.

(51) Int. Cl.

| | | |
|---|---|---|
| *A61B 5/026* | (2006.01) | |
| *A61B 5/0295* | (2006.01) | |
| *A61B 5/1455* | (2006.01) | |
| *H01L 25/16* | (2023.01) | |
| *H01L 31/0232* | (2014.01) | |
| *H01L 31/16* | (2006.01) | |

(52) U.S. Cl.
CPC ........ *A61B 5/0295* (2013.01); *A61B 5/14551* (2013.01); *A61B 5/681* (2013.01); *H01L 25/167* (2013.01); *H01L 31/02327* (2013.01); *H01L 31/16* (2013.01); *A61B 2562/0238* (2013.01); *A61B 2562/0242* (2013.01); *A61B 2562/046* (2013.01)

(56) References Cited

U.S. PATENT DOCUMENTS

| | | |
|---|---|---|
| 5,483,261 A | 1/1996 | Yasutake |
| 5,488,204 A | 1/1996 | Mead et al. |
| 5,759,156 A | 6/1998 | Hayakawa et al. |
| 5,782,237 A | 7/1998 | Casciani |
| 5,825,352 A | 10/1998 | Bisset et al. |
| 5,835,079 A | 11/1998 | Shieh |
| 5,880,411 A | 3/1999 | Gillespie et al. |
| 6,031,603 A * | 2/2000 | Fine .................. A61B 5/14552 356/41 |
| 6,115,621 A | 9/2000 | Chin |
| 6,188,391 B1 | 2/2001 | Seely et al. |
| 6,277,067 B1 | 8/2001 | Blair |
| 6,310,610 B1 | 10/2001 | Beaton et al. |
| 6,323,846 B1 | 11/2001 | Westerman et al. |
| 6,343,233 B1 | 1/2002 | Chin et al. |
| 6,491,647 B1 | 12/2002 | Bridger |
| 6,529,754 B2 | 3/2003 | Kondo |
| 6,533,729 B1 | 3/2003 | Khair et al. |
| 6,587,703 B2 | 7/2003 | Cheng et al. |
| 6,594,513 B1 | 7/2003 | Jobsis et al. |
| 6,690,387 B2 | 2/2004 | Zimmerman et al. |
| 6,859,658 B1 | 2/2005 | Krug |
| 7,015,894 B2 | 3/2006 | Morohoshi |
| 7,139,076 B1 | 11/2006 | Marbach |
| 7,184,064 B2 | 2/2007 | Zimmerman et al. |
| 7,204,606 B2 | 4/2007 | Brass et al. |
| 7,372,778 B2 | 5/2008 | Klopfenstein et al. |
| 7,450,799 B2 | 11/2008 | Selbrede et al. |
| 7,616,110 B2 | 11/2009 | Crump et al. |
| 7,643,153 B2 | 1/2010 | de Boer et al. |
| 7,663,607 B2 | 2/2010 | Hotelling et al. |
| 7,676,253 B2 | 3/2010 | Rarldan, Jr. |
| 7,729,748 B2 | 6/2010 | Florian |
| 7,740,589 B2 | 6/2010 | Maschke et al. |
| 7,890,153 B2 | 2/2011 | Hoarau |
| 8,005,624 B1 | 8/2011 | Starr |
| 8,086,301 B2 | 12/2011 | Cho et al. |
| 8,135,447 B2 | 3/2012 | Kondoh et al. |
| 8,203,704 B2 | 6/2012 | Merritt et al. |
| 8,252,369 B2 | 8/2012 | Jiang |
| 8,378,811 B2 | 2/2013 | Crump et al. |
| 8,380,272 B2 | 2/2013 | Barrett et al. |
| 8,479,122 B2 | 7/2013 | Hotelling et al. |
| 8,588,878 B2 | 11/2013 | Li et al. |
| 8,618,930 B2 | 12/2013 | Papadopoulos et al. |
| 8,704,152 B2 | 4/2014 | Svajda et al. |
| 8,788,002 B2 | 7/2014 | Leboeuf et al. |
| 8,803,745 B2 | 8/2014 | Dabov |
| 8,805,302 B2 | 8/2014 | Pantfoerder |
| 8,948,832 B2 | 2/2015 | Hong et al. |
| 8,974,396 B1 | 3/2015 | Brady |
| 8,998,815 B2 | 4/2015 | Venkatraman et al. |
| 9,008,742 B2 | 4/2015 | Naganuma et al. |
| 9,049,998 B2 | 6/2015 | Brumback et al. |
| 9,113,793 B2 | 8/2015 | Terumoto et al. |
| 9,314,197 B2 | 4/2016 | Eisen et al. |
| 9,322,901 B2 | 4/2016 | Kerness et al. |
| 9,326,711 B2 | 5/2016 | Kracker et al. |
| 9,348,322 B2 | 5/2016 | Fraser et al. |
| 9,392,946 B1 | 7/2016 | Sarantos |
| 9,449,955 B2 | 9/2016 | Tu et al. |
| 9,506,802 B2 | 11/2016 | Chu et al. |
| 9,526,421 B2 | 12/2016 | Papadopoulos et al. |
| 9,596,990 B2 | 3/2017 | Park et al. |
| 9,737,221 B2 | 8/2017 | Sato |
| 9,826,905 B2 | 11/2017 | Addison et al. |
| 10,058,254 B2 | 8/2018 | Fei |
| 10,060,788 B2 | 8/2018 | Fei |
| 10,092,197 B2 | 10/2018 | Han et al. |
| 10,165,951 B2 | 1/2019 | Rimoldi et al. |
| 10,172,529 B2 | 1/2019 | Fei |
| 10,180,235 B2 | 1/2019 | Rudmann et al. |
| 10,206,589 B2 | 2/2019 | Walker |
| 10,219,729 B2 | 3/2019 | Kintz et al. |
| 10,247,670 B2 | 4/2019 | Ness et al. |
| 10,265,003 B2 | 4/2019 | Eguchi et al. |
| 10,265,024 B2 | 4/2019 | Lee et al. |
| 10,266,320 B2 | 4/2019 | McKenzie et al. |
| 10,646,143 B2 | 5/2020 | Wang |
| 10,687,717 B1 | 6/2020 | Peterson |
| 10,732,574 B2 | 8/2020 | Shim et al. |
| 10,907,844 B2 | 2/2021 | Ribbich et al. |
| 10,918,322 B2 | 2/2021 | Shao et al. |
| 11,627,887 B2 | 4/2023 | Peterson et al. |
| 2002/0042558 A1 | 4/2002 | Mendelson |
| 2002/0188210 A1 | 12/2002 | Aizawa |
| 2004/0032728 A1 | 2/2004 | Galli |
| 2005/0230603 A1 | 10/2005 | Langland |
| 2006/0197753 A1 | 9/2006 | Hotelling |
| 2008/0004510 A1 | 1/2008 | Tanzawa et al. |
| 2008/0297788 A1 | 12/2008 | Rowe et al. |
| 2009/0018452 A1 | 1/2009 | Sugiura et al. |
| 2009/0182208 A1 | 7/2009 | Cho et al. |
| 2009/0326346 A1 | 12/2009 | Kracker et al. |
| 2010/0056934 A1 | 3/2010 | Cho et al. |
| 2010/0113948 A1 | 5/2010 | Yang et al. |
| 2011/0077537 A1 | 3/2011 | Ebara et al. |
| 2011/0260176 A1 | 10/2011 | Onoe et al. |
| 2012/0078116 A1 | 3/2012 | Yamashita |
| 2012/0223231 A1 | 9/2012 | Nijaguna |
| 2013/0006074 A1 | 1/2013 | Pologe |
| 2013/0046192 A1 | 2/2013 | Lin et al. |
| 2013/0060098 A1 | 3/2013 | Thomsen |
| 2013/0289414 A1 | 10/2013 | Adibnazari et al. |
| 2013/0324866 A1 | 12/2013 | Gladshtein |
| 2014/0024905 A1 | 1/2014 | Sarrafzadeh et al. |
| 2014/0183342 A1 * | 7/2014 | Shedletsky ........... G06F 1/1637 250/215 |
| 2014/0187992 A1 | 7/2014 | Wilmering |
| 2014/0288435 A1 | 9/2014 | Richards et al. |
| 2015/0065830 A1 | 3/2015 | Karp et al. |
| 2015/0234188 A1 | 8/2015 | Lee |
| 2016/0058312 A1 * | 3/2016 | Han ...................... G01N 21/55 600/479 |
| 2016/0073954 A1 | 3/2016 | Meitav |
| 2016/0113530 A1 | 4/2016 | Nagahiro et al. |
| 2016/0198962 A1 | 7/2016 | Park et al. |
| 2016/0206221 A1 | 7/2016 | Kim et al. |
| 2016/0235364 A1 | 8/2016 | Yoshida |
| 2016/0235369 A1 | 8/2016 | Horikawa et al. |
| 2016/0242659 A1 | 8/2016 | Yamashita et al. |
| 2016/0310027 A1 * | 10/2016 | Han ............... A61B 5/6898 |
| 2017/0164848 A1 * | 6/2017 | Nadeau ............ A61B 5/14552 |
| 2017/0202466 A1 | 7/2017 | Paulussen et al. |
| 2017/0347902 A1 | 12/2017 | Van Gool |
| 2018/0049702 A1 | 2/2018 | Tsai |
| 2018/0054077 A1 | 2/2018 | Brzezinski et al. |
| 2018/0113911 A1 | 4/2018 | Ikeda |
| 2019/0000331 A1 | 1/2019 | Han |
| 2019/0018173 A1 * | 1/2019 | Kim ...................... G02B 5/208 |

(56) References Cited

U.S. PATENT DOCUMENTS

| | | |
|---|---|---|
| 2019/0069781 A1 | 3/2019 | Kim |
| 2019/0086331 A1 | 3/2019 | Han et al. |
| 2019/0090766 A1 | 3/2019 | Block et al. |
| 2021/0161444 A1 | 6/2021 | Shao et al. |
| 2023/0204506 A1 | 6/2023 | Han et al. |

FOREIGN PATENT DOCUMENTS

| | | |
|---|---|---|
| CN | 101730503 | 6/2010 |
| CN | 103327894 | 9/2013 |
| CN | 103610467 | 3/2014 |
| CN | 205054183 | 3/2016 |
| EP | 1946697 | 7/2008 |
| EP | 2992821 | 3/2016 |
| EP | 3117762 | 1/2017 |
| EP | 3111834 | 4/2017 |
| GB | 2524160 | 9/2015 |
| GB | 2547736 | 8/2017 |
| JP | 57093039 | 6/1982 |
| JP | H0231734 | 2/1990 |
| JP | H11128184 | 5/1999 |
| JP | 2000163031 | 6/2000 |
| JP | 2002342033 | 11/2002 |
| JP | 2002345760 | 12/2002 |
| JP | 2005040608 | 2/2005 |
| JP | 2008264302 | 11/2008 |
| JP | 2011251007 | 12/2011 |
| JP | 2013094482 | 5/2013 |
| JP | 2013118922 | 6/2013 |
| JP | 2016158701 | 9/2016 |
| KR | 0100091592 | 8/2010 |
| KR | 20140145392 | 12/2014 |
| TW | 201806548 | 3/2018 |
| WO | WO 95/020757 | 8/1995 |
| WO | WO 01/117420 | 3/2001 |
| WO | WO 07/122375 | 11/2007 |
| WO | WO 09/139029 | 11/2009 |
| WO | WO 12/011029 | 1/2012 |
| WO | WO 12/158384 | 11/2012 |
| WO | WO 12/158386 | 11/2012 |
| WO | WO 12/158387 | 11/2012 |
| WO | WO 14/043410 | 3/2014 |
| WO | WO 14/066791 | 5/2014 |
| WO | WO 15/084375 | 6/2015 |
| WO | WO 15/094378 | 6/2015 |
| WO | WO 15/122980 | 8/2015 |
| WO | WO 16/032682 | 3/2016 |
| WO | WO 19/067196 | 4/2019 |

OTHER PUBLICATIONS

Lee, S.K. et al. (Apr. 1985). "A Multi-Touch Three Dimensional Touch-Sensitive Tablet," Proceedings of CHI: ACM Conference on Human Factors in Computing Systems, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

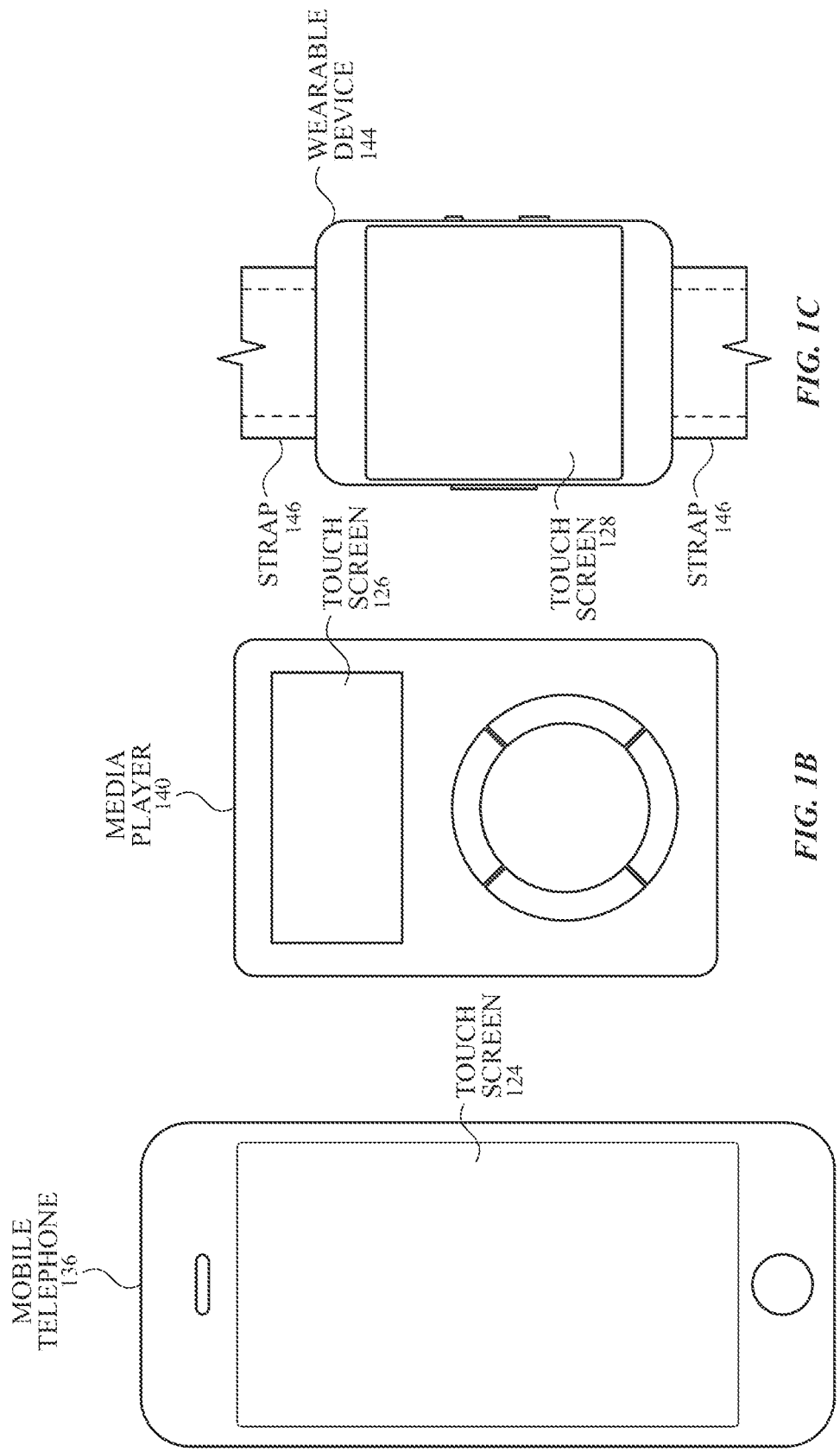

CONCENTRIC ARCHITECTURE FOR OPTICAL SENSING

CROSS-REFERENCE TO RELATED APPLICATIONS

This application is a continuation of U.S. patent application Ser. No. 16/126,970, filed Sep. 10, 2018, which claims the benefit of U.S. Provisional Patent Application No. 62/563,594, filed Sep. 26, 2017, the entire disclosures of which are incorporated herein by reference in their entirety.

FIELD

This relates generally to architectures for optical sensing. More particularly, the disclosure relates to architectures for an optical sensing unit including a plurality of light detectors arranged in a concentric manner around a plurality of light emitters.

BACKGROUND

A photoplethysmogram (PPG) signal can be measured by optical sensing systems to derive corresponding physiological signals (e.g., pulse rate). In a basic form, the optical sensing systems can employ a light emitter that emits light through an aperture and/or window into the user's tissue. In addition, a light detector can be included to receive light through an aperture and/or window. The light received by the light detector can be light that has returned (e.g., reflected or scattered) and exited the tissue. In some instances, optical losses due to one or more components in the system may affect the determination of the user's physiological information.

SUMMARY

This disclosure relates to an electronic device configured for optical sensing having a concentric architecture and methods for operation thereof. The concentric architecture can include a plurality of light detectors arranged in a concentric manner around a plurality of light emitters. The plurality of light emitters can include a plurality of first light emitters emitting at a first wavelength range (e.g., visible wavelengths) and one or more second light emitters emitting at a second wavelength range (e.g., infrared wavelengths). In some examples, at least one second light emitter can be located in the center of the device, and each light detector can be located the same separation distance from the at least one second light emitter. Each light detector can be arranged such that the separation distance from the centrally located second light emitter can be greater than the separation distance from a first light emitter.

Examples of the disclosure further include a selective transparent layer overlaying the plurality of light detectors. The selective transparent layer can include a plurality of first sections transparent to a second wavelength range (e.g., infrared wavelengths) and non-transparent to a first wavelength ranges (e.g., visible wavelengths). The selective transparent layer can further include a plurality of second sections transparent to the second wavelength range. In some examples, a Fresnel lens can be located in a corresponding region of the first and second light emitters. The Fresnel lens can include a plurality of regions, such as a first region and a second region. The first region can be located in the field of view(s) of the first light emitter(s), and the second region can be located in the field of view(s) of the second light emitter(s). The plurality of regions of the Fresnel lens may have different optical (e.g., percent transmission, amount of collimation, etc.) properties.

Methods for operating the optical sensing unit can include associating the plurality of light detectors to one or more channels. Each light emitter is sequentially activated to emit light, and the one or more channels can further sequentially measure light from the given light emitter. In some examples, the association of the one or more channels can be dynamically changed. For example, during a first time, all of the plurality of light detectors can be associated to a single channel. The system can dynamically change, during a second time, to the plurality of light detectors being associated to multiple channels. In some examples, the device can be configured to perform multiple measurement types (e.g., primary and secondary measurements) as part of a sampling procedure, where the primary measurements can include readings using a first set of operating conditions of the PPG sensor unit, and the secondary measurements can use a different second set of operating conditions of the PPG sensor unit. The single channel can be used for the primary measurements, and the multiple channels can be used for the secondary measurements, for example.

BRIEF DESCRIPTION OF THE DRAWINGS

FIGS. 1A-1C illustrate systems in which examples of the disclosure can be implemented.

DETAILED DESCRIPTION

Figure 2A:
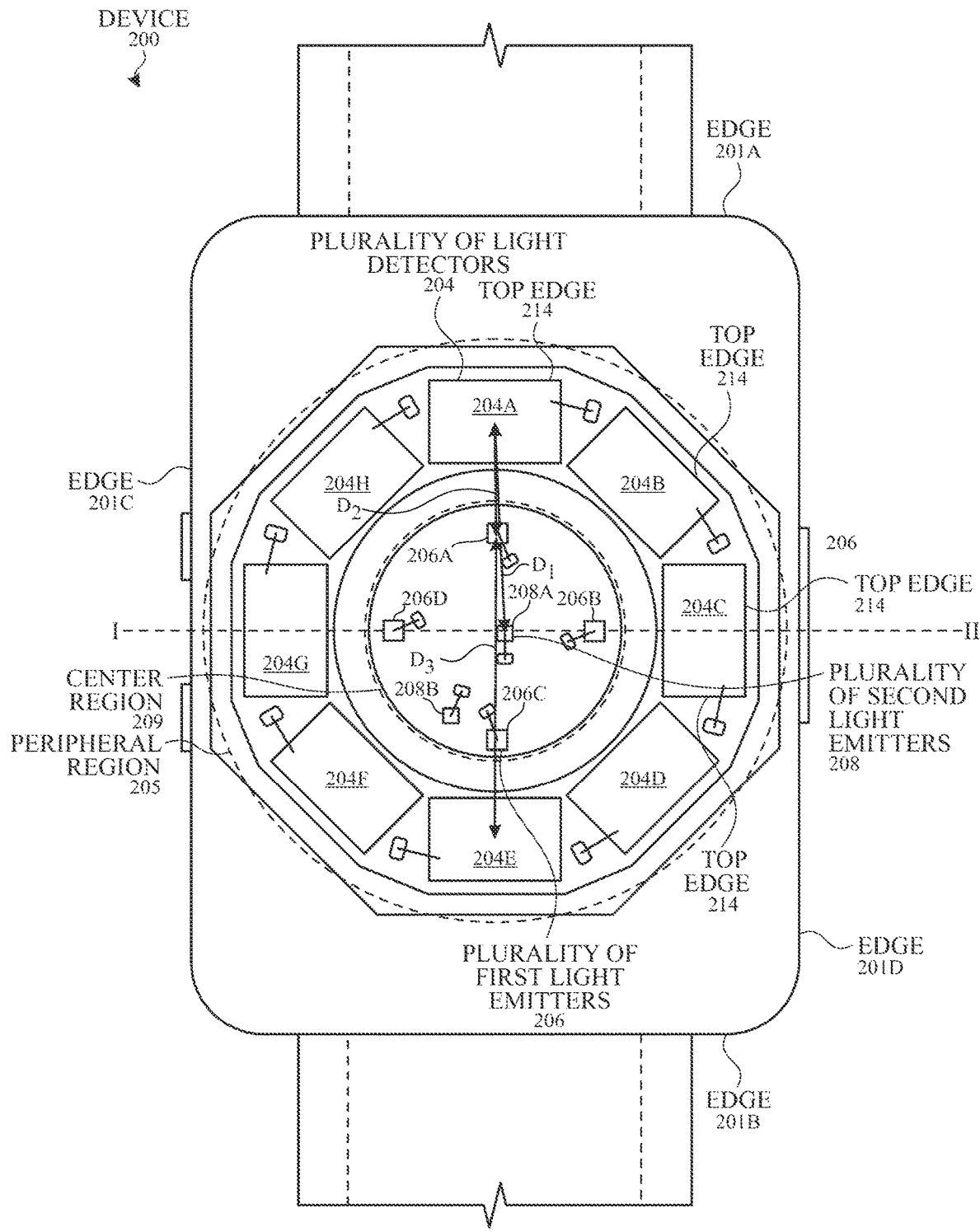
FIG. 2A illustrates a top view of an exemplary electronic device including a concentric architecture for optical sensing according to examples of the disclosure.

In the following description of examples, reference is made to the accompanying drawings in which it is shown by way of illustration specific examples that can be practiced. It is to be understood that other examples can be used and structural changes can be made without departing from the scope of the various examples. Numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

A photoplethysmographic (PPG) signal can be measured by an optical sensing system to derive corresponding physiological signals (e.g., pulse rate). Such optical sensing systems can be designed to be sensitive to changes in a user's tissue that can result from fluctuations in the amount or volume of blood or blood oxygen in the vasculature of the user. In a basic form, optical sensing systems can employ a light emitter or light emitter that emits light through an aperture and/or window into the user's tissue. The system can further include a light detector to receive return light (i.e., light that has reflected and/or scattered and exited the tissue) through the same or another aperture and/or window. The PPG signal is the amplitude of return light that is modulated with volumetric change in blood volume in the tissue. The light emitters and light emitters in the optical sensing system can be arranged in a concentric architecture.

This disclosure relates to an electronic device configured for optical sensing having a concentric architecture and methods for operation thereof. The concentric architecture can include a plurality of light detectors arranged in a concentric manner around a plurality of light emitters. The plurality of light emitters can include a plurality of first light emitters emitting at a first wavelength range (e.g., visible wavelengths) and one or more second light emitters emitting at a second wavelength range (e.g., infrared wavelengths). In some examples, at least one second light emitter can be located in the center of the device, and each light detector can be located the same separation distance from the at least one second light emitter. Each light detector can be arranged such that the separation distance from the centrally located second light emitter can be greater than the separation distance from a first light emitter.

Examples of the disclosure further include a selective transparent layer overlaying the plurality of light detectors. The selective transparent layer can include a plurality of first sections transparent to a second wavelength range (e.g., infrared wavelengths) and at least partially non-transparent to a first wavelength ranges (e.g., visible wavelengths). The selective transparent layer can further include a plurality of second sections transparent to the second wavelength range. In some examples, a Fresnel lens can be located in a corresponding region of the first and second light emitters. The Fresnel lens can include a plurality of regions, such as a first region and a second region. The first region can be located in the field of view(s) of the first light emitter(s), and the second region can be located in the field of view(s) of the second light emitter(s). The plurality of regions of the Fresnel lens may have different optical (e.g., percent transmission, amount of collimation, etc.) properties.

Methods for operating the optical sensing unit can include associating the plurality of light detectors to one or more channels. Each light emitter is sequentially activated to emit light, and the one or more channels can further sequentially measure light from the given light emitter. In some examples, the association of the one or more channels can be dynamically changed. For example, during a first time, all of the plurality of light detectors can be associated to a single channel. The system can dynamically change, during a second time, to the plurality of light detectors being associated to multiple channels. In some examples, the device can be configured to perform multiple measurement types (e.g., primary and secondary measurements) as part of a sampling procedure, where the primary measurements can include readings using a first set of operating conditions of the PPG sensor unit, and the secondary measurements can use a different second set of operating conditions of the PPG sensor unit. The single channel can be used for the primary measurements, and the multiple channels can be used for the secondary measurements, for example.

Representative applications of the apparatus and methods according to the present disclosure are described in this section. These examples are being provided solely to add context and aid in the understanding of the described examples. It will thus be apparent to one skilled in the art that the described examples may be practiced without some or all of the specific details. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the optical layers, the optical films, the lenses, the window systems, the concentric architecture, and/or methods for detecting a PPG signal as will be disclosed.

Exemplary Configuration of the Optical Sensing Unit

FIG. 2A illustrates a top view of an exemplary electronic device including a concentric architecture for optical sensing according to examples of the disclosure. The top view in FIG. 2A can be viewed as the underside of wearable device 144 of FIG. 1C, for example. Further, the top view in FIG. 2A includes a partial top view of device without a selective transparent layer (discussed below) overlaid.

Device 200 can include a plurality of light detectors 204A, 204B, 204C, 204D, 204E, 204F, 204G, and 204H (collectively referred to as plurality of light detectors 204); a plurality of first light emitters 206A, 206B, 206C, and 206D (collectively referred to as plurality of first light emitters 206); and a plurality of second light emitters 208A and 208B (collectively referred to as plurality of second light emitters 208). The device 200 can be situated such that the plurality of light detectors 204, the plurality of first light emitters 206, and second light emitter 208 are proximate to the user's skin. For example, the device 200 can be held in a user's hand or strapped to a user's wrist, among other possibilities.

The device can include a plurality of regions such as the center region 209 and the peripheral region 205. The center region 209 can be separated from the peripheral region 205 by an optical isolation (e.g., optical isolation 216), where the peripheral region 205 can be located closer to the edges (e.g., edge 201C) of the device 200 than the center region 209. For example, the center region 209 can include a plurality of light emitters (e.g., first light emitters 206 and second light emitters 208). In some examples, the plurality of first light emitters 206 can be located closer to the peripheral region than at least one second light emitter 208

(e.g., second light emitter 208A). In some examples, at least one second light emitter 208 (e.g., second light emitter 208A) can be located in the center of the center region 209. In some examples, the plurality of first light emitters 206 can be configured to emit a different range(s) of wavelengths (e.g., green wavelengths) than the second light emitter(s) 208 (e.g., second light emitters can be configured to emit infrared wavelengths). The peripheral region 205 can partially or entirely surround the center region 209.

In some examples, the separation distances and locations of the light detectors and light emitters can optimized for different types of measurements (e.g., primary and secondary measurements). For example, the second light emitter 208A can be located in the center of device 200 and can be configured to emit infrared light for detecting one type of information. The center of device 200 can be such that the distances from second light emitter 208A to the edges of device 200 along the same direction (e.g., left-to-right and/or top-to-bottom) are the same. For example, the distance from the top edge 201A of the device and second light emitter 208A can be the same as the distance from the bottom edge 201B of the device. The distance from the left edge 201C of the device and second light emitter 208A can be the same as the distance from the right edge 201D of the device. Optionally, device 200 can include second light emitter 208B also used for detecting the same type of information as the second light emitter 208A.

The plurality of first light emitters 206 can be placed closer to the peripheral region 205. For example, the plurality of first light emitters 206 can include four light emitters: first light emitter 206A, first light emitter 206B, first light emitter 206C, and first light emitter 206D, which can be arranged to form a square, rectangle, quadrilateral, or the like. For example, the plurality of first light emitters 206 can be arranged in a square where the separation distances between first light emitter 206A and first light emitter 206B, between first light emitter 206B and first light emitter 206C, between first light emitter 206C and first light emitter 206D, and between first light emitter 206D and first light emitter 206A can be the same. In some examples, the separation distances between each first light emitter 206 and the center second light emitter 208A can be the same. Although the figure illustrates the plurality of first light emitters 206 as located the same separation distance from optical isolation 216, examples of the disclosure can include the light emitters being separated at varying distances. Further, examples of the disclosure are not limited to the light emitters located in a square-like arrangement, and pairs of first and second light emitters are not limited to having the same separation distances.

The peripheral region 205 can be located around (partially or entirely) the center region 209. The plurality of light detectors 204 can be radially arranged in the peripheral region 205. In some examples, a radial arrangement can include the plurality of light detectors 204 as oriented with an angle of a given edge dependent on the location in the peripheral region 205, where each light detector 204 has the same or similar shape. For example, an angle of a top edge 214 (e.g., edge of the light detector closest to the edges of the device) of light detector 204A and light detector 204E can be at 0°. Top edge 214 of light detector 204B and/or light detector 204F can be 45° relative to the top edge 214 of light detector 204A and/or light detector 204E. Top edge 214 of light detector 204D and/or light detector 204H can be −45° relative to the top edge 214 of light detector 204A and/or light detector 204E. Top edge 214 of light detector 204C and/or light detector 204G can be 90° or −90° relative to top edge 214 of light detector 204A and/or light detector 204E. In this manner, the top edges 214 of two or more light detectors 204 can have different angles of orientation.

The relative arrangement of the light emitters and light detectors can be such that the distance (i.e., separation distance $D_2$) between a first light emitter 206 (e.g., first light emitter 206A) and its closest light detector 204 (e.g., light detector 204A) can be less than the distance (i.e., separation distance $D_1$) between a second light emitter 208 (e.g., second light emitter 208A) and the same light detector 204. In instances, the first light emitter 206A can be a LED that emits visible light (e.g., green light) that has a separation distance $D_2$ to one light detector 204A that is shorter than the separation distances to the other light detectors, such as the light detectors 204B-204H. The term "separation distance" means the distance measured from the center of one component to the center of the other component. In some examples, the separation distance between a first light emitter 206 and its closest neighboring light detectors 204 can be the same. Additionally, the distance (e.g., separation distance $D_3$) between the same closest first light emitter 206 (e.g., first light emitter 206A) and another light detector (e.g., light detector 204E) can be greater than both the separation distance $D_1$ and the separation distance $D_2$, as illustrated in the figure.

In some examples, the second light emitter 208A can be an infrared light emitter configured for one type of measurement, and the first light emitter 206A can be a visible (e.g., green wavelengths) light emitter configured for another type of measurement. In some examples, the light detectors associated with the separation distance $D_1$ and the separation distance $D_3$ can have the same angle of orientation. For example, the light detector 204A and the light detector 204E can both have a top edge 214 orientated at 0°.

In some examples, each light detector can be configured such that an edge "aligns" with a light emitter. For example, the center of the first light emitter 206A can be along the same y-plane as the center of the light detector 204A. In this manner, the separation distance $D_2$ between centers of a first light emitter (e.g., the first light emitter 206A) and its closest light detector (e.g., light detector 204A) is less than the separation distances between the center of the same first light emitter and others of the plurality of light detectors 204.

Figure 2B:
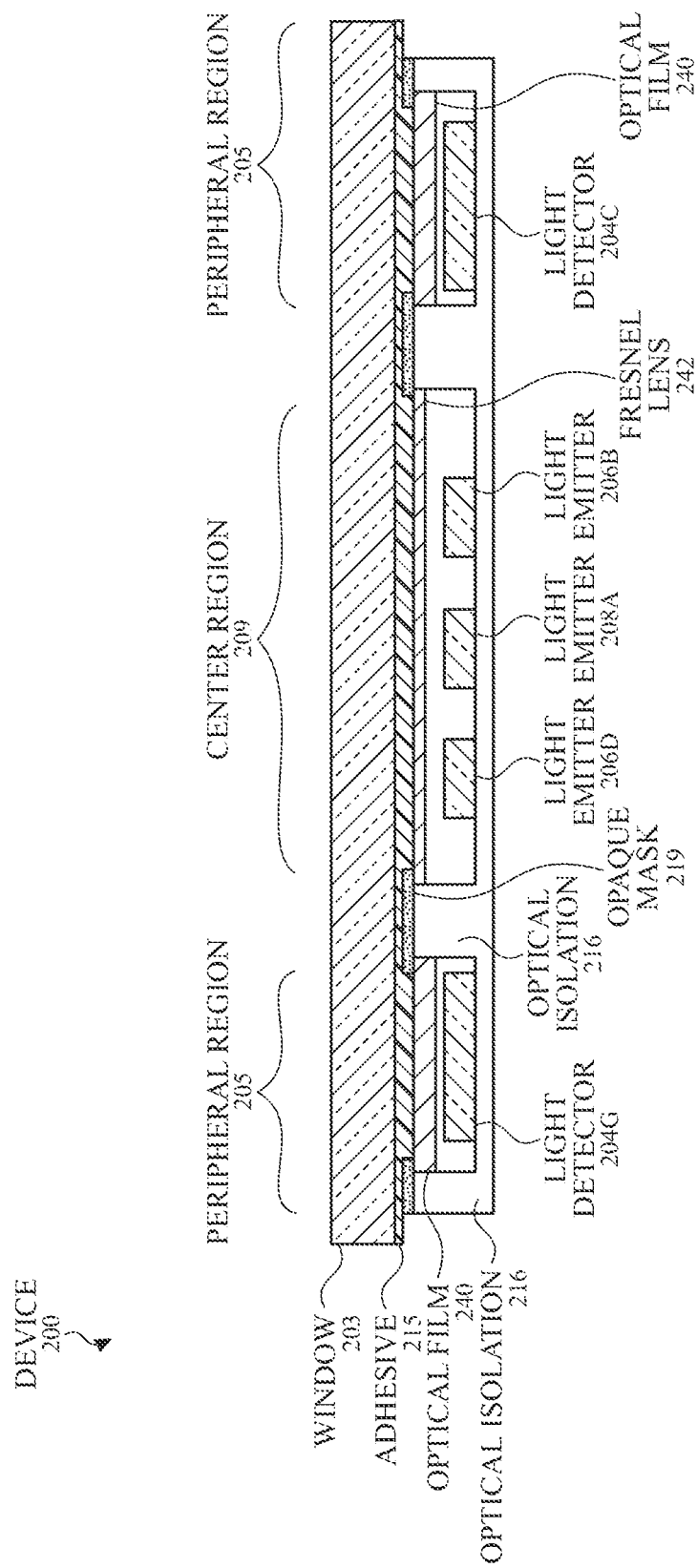
FIG. 2B illustrates the cross-sectional view of FIG. 2A along line I-II according to examples of the disclosure.
Figure 2C:
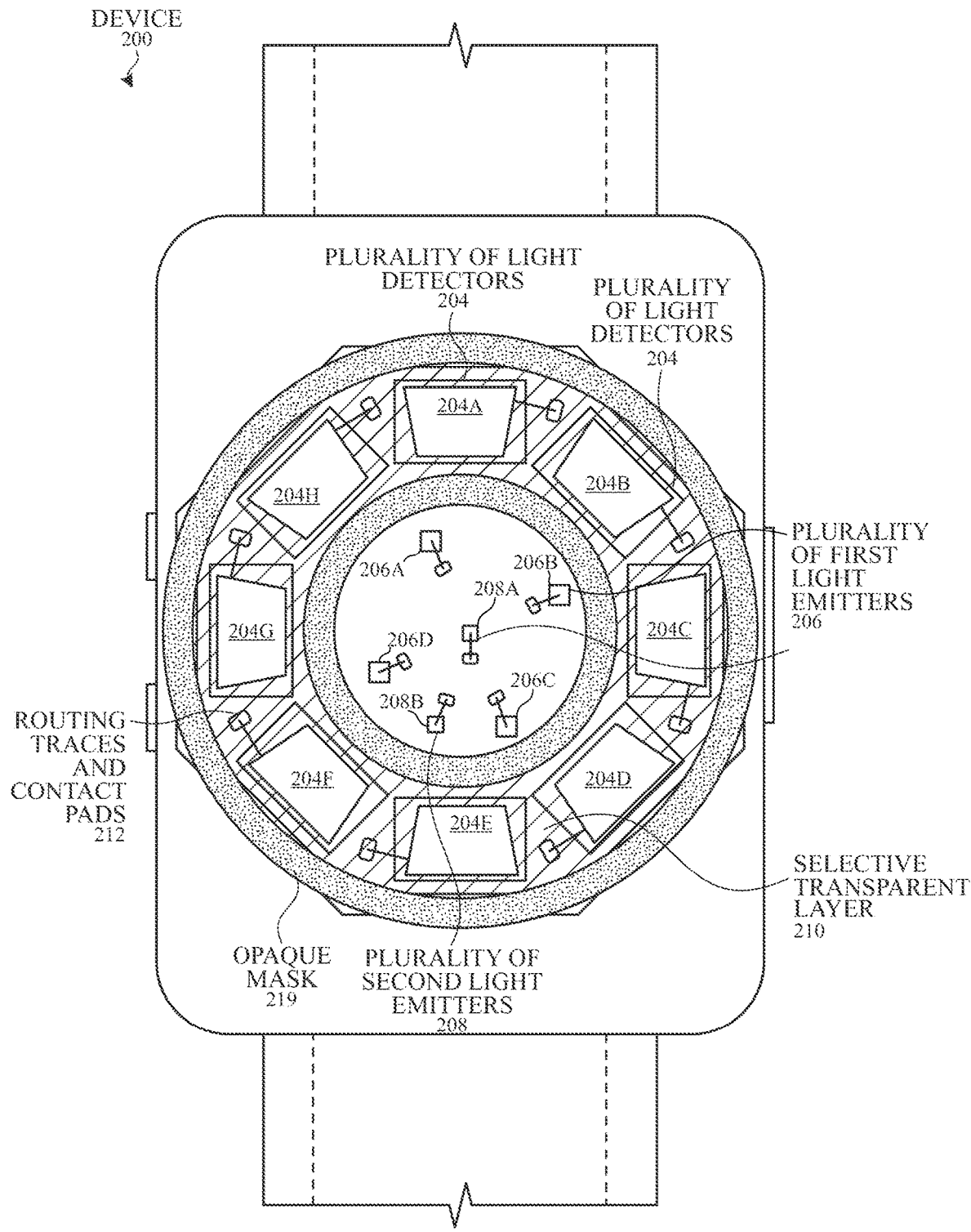
FIG. 2C illustrates a top view of an exemplary concentric architecture including a selective transparent layer overlaid according to examples of the disclosure.

In other examples, the first light emitter 206A can be located between the edges of adjacent light detectors 204A and 204H, as shown in FIG. 2C. That is, the radial angle of first light emitter 206A can be the same as the radial angle of the edges of light detector 204A and light detector 204H. In this manner, the separation distances between the center of a light emitter (e.g., first light emitter 206A) and the center of its two closest light detectors (e.g., light detector 204A and 204H and/or two adjacent light detectors) can be the same. Although the figure illustrates eight light detectors 204 and four first light emitters 206, examples of the disclosure can include any number of light detectors and any number of light emitters. Further, although the figure illustrates the light detectors 204 as having rectangular-shaped detection areas and the light emitters as having square-shared emitting areas, examples of the disclosure can include any shape.

The device 200 can include one or more components for enhanced optical collection, signal generation, and/or reduced noise. FIG. 2B illustrates the cross-sectional view of FIG. 2A along line I-II. The one or more components can include optical isolation 216, optical film 240, and Fresnel lens 242. To prevent or reduce optical crosstalk between the plurality of light detectors 204 and the plurality of first light emitters 206, optical isolation 216 can be a wall located between the plurality of light detectors 204 and the plurality of first light emitters 206. The optical isolation 216 can thereby define the cavity of the light emitters, separate from the cavity or cavities of the light detectors. The optical isolation 216 can be located in the center region 209 and/or in the peripheral region 205. In some examples, the optical isolation 216 located in center region 209 can include the same material (or be formed from a continuous piece of material) as included in the optical isolation 216 located in peripheral region 205. In some instances, the optical isolation 216 can be a concentric ring. In some examples, the optical isolation 216 may be different from other types of isolation that may be included in the device. Optical isolation 216 may collectively form at least two cavities which the light emitters and light sensors may be located within. Other types of isolation may include, but are not limited to, optical, electrical, and/or mechanical isolation of the optical sensing system from other components (e.g., a display or a touch screen) included in the device.

The optical film 240 can be a film configured for light restriction (discussed in detail below). The optical film 240 can at least partially overlay the section of window 203 corresponding to light passing through to at least one light detector 204. In some examples, device 200 can include one section of optical film 240 disposed over each light detector 204. The optical film 240 can have other arrangements such as being attached to a window, being disposed on a window, being disposed on a detector, and the like. In some examples, a single (e.g., ring-shaped) optical film 240 can be disposed over a plurality (including all) of light detectors 204. In some examples, the edges of optical film 240 can extend to (e.g., contact) the optical isolation 216.

The Fresnel lens 242 can be a lens configured to direct and/or focus light emitted by the light emitters. The Fresnel lens 242 can at least partially overlay the section of window 203 corresponding to light passing through from the plurality of first light emitters 206 and/or the second light emitter(s) 208. That is, the Fresnel lens 242 can be located in the field of view of the plurality of first light emitters 206 and the field of view of the plurality of second light emitters 208. The Fresnel lens 242 can be configured for one or more targeted types of measurements. In some examples, the Fresnel lens 242 can be configured for obscuration of the light emitters. For example, the features of the Fresnel lens 242 can be based on achieving optimal measurements associated with the second light emitter 208 and associated with the plurality of first light emitters 206, while also reducing the visibility of the light emitters.

Additionally, device 200 can include one or more layers for reducing visibility of other components. Opaque mask 219 can be configured to reduce visibility optical isolation 216 and/or the edge of optical film 240 by being opaque at one or more wavelengths (e.g., the wavelengths being measured by the device). In some examples, a portion of opaque mask 219 can extend past the walls of the cavities (e.g., created by optical isolation 216). In some examples, the opaque mask 219 and the optical isolation 216 can include the same materials and/or functions (e.g., act as an optical isolation and/or cosmetic layer). At least one end of the opaque mask 219 and/or the optical isolation 216 can be located at or in close proximity to the internal surface (i.e., surface furthest from the exterior surface of the housing of device 200) of window 203. The device 200 further can include an adhesive 215 configured to adhere one or more components (e.g., optical film 240, opaque mask 219, etc.) to the window 203.

Figure 2D:
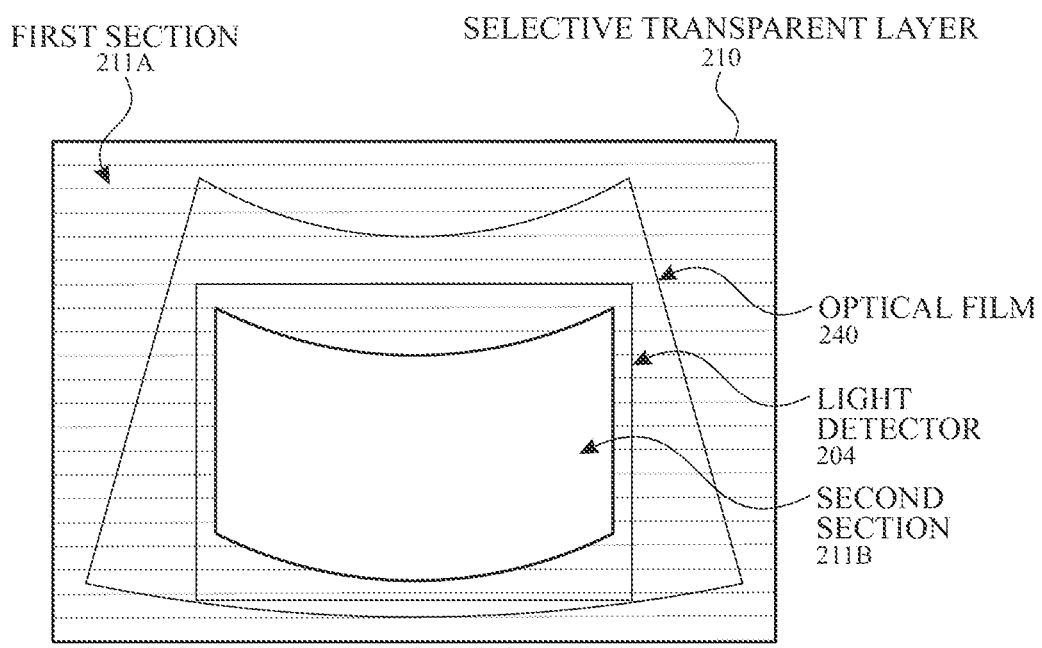
FIG. 2D illustrates an enlarged view of an exemplary selective transparent layer overlaying a single light detector according to examples of the disclosure.

FIG. 2C illustrates a top view of the concentric architecture including the selective transparent layer overlaid according to examples of the disclosure. FIG. 2D illustrates an enlarged view of the selective transparent layer overlaying a single light detector according to examples of the disclosure. A selective transparent layer 210 can be located in a peripheral region (e.g., peripheral region 205 illustrated in FIG. 2A). The selective transparent layer 210 can be configured to conceal routing traces and the contact pads 212 and/or edges of the plurality of light detectors 204. In this manner, the selective transparent layer 210 can be located between the optical film 240 and the adhesive 215. The selective transparent layer 210 can include one or more first sections 211A of material that is at least partially transparent to a second wavelength range (e.g., infrared wavelengths) of light, wherein the transparency can be configured to allow light to reach the plurality of light detectors 204 for, e.g., a secondary measurement. The selective transparent layer 210 can also include one or more second sections 211B overlaying a central portion of each light detector 204 to allow light of a first wavelength range (e.g., visible wavelengths) to reach the plurality of light detectors 204 for, e.g., a primary measurements. The one or more second sections 211B overlaying the central portion can include material transparent to the second wavelength range or may be omitted material (e.g., an opening). In some instances, the one or more second sections 211B can also be transparent to the first wavelength range.

In some examples, the first section(s) 211A can be partially transparent (i.e., partially blocks) a first wavelength range and fully transparent to a second wavelength range.

The selective transparent layer 210 can be located anywhere in the field of view of the plurality of light detectors 204. For example, the selective transparent layer 210 can be located between the optical film 240 and the window 203. Examples of the disclosure can include the selective transparent layer 210 as being a layer separate from the windows 203. In other instances, the selective transparent layer 210 can be formed in the window 203.

Figure 2E:
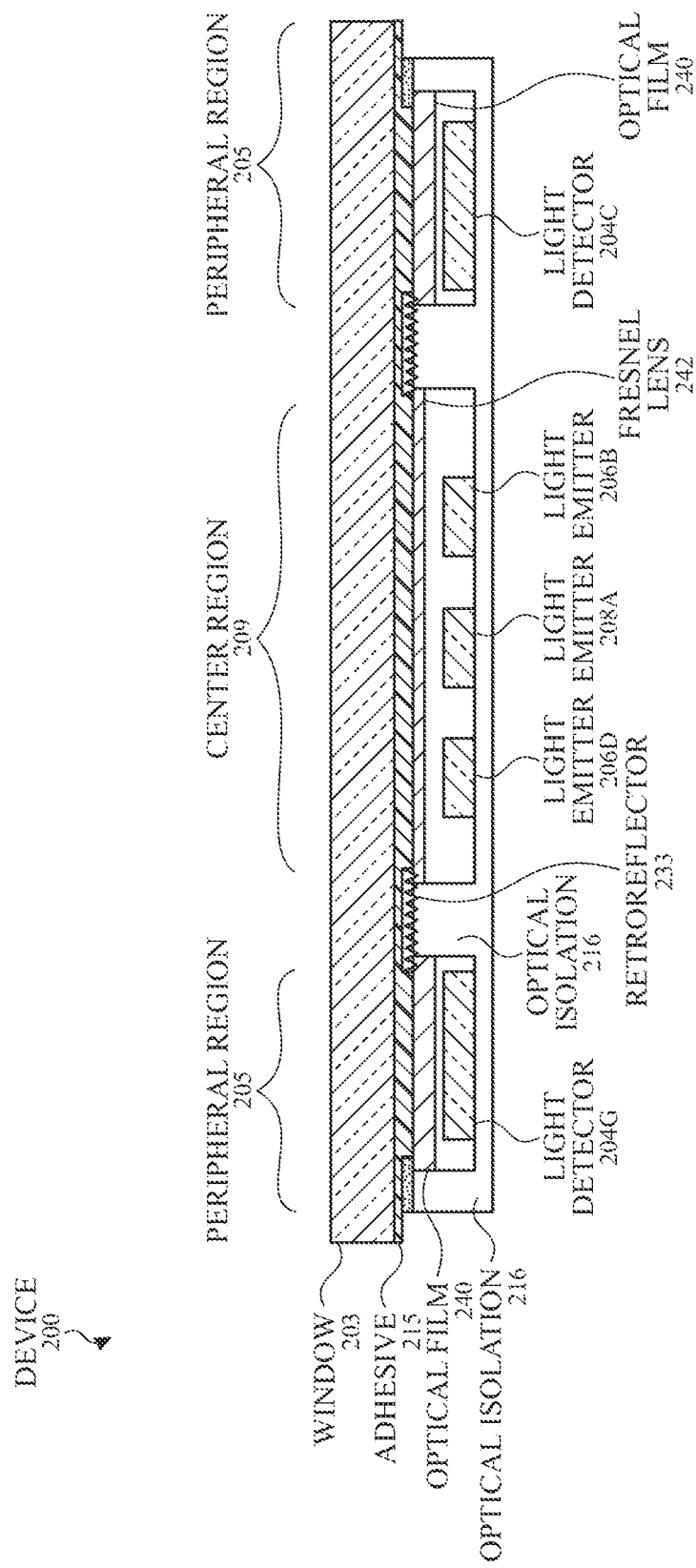
FIG. 2E illustrates a cross-sectional view of an exemplary electronic dev ice including a concentric architecture and a retroreflector according to examples of the disclosure.

In some examples, the device can include one or more components configured to redirect light that may not include physiological information, thereby preventing the unwanted light from reaching the light detector. FIG. 2E illustrates a cross-sectional view of an exemplary electronic device including a concentric architecture and a retroreflector according to examples of the disclosure. The device 200 can include a retroreflector 233 located proximate to the optical isolation 216. In some instances, the retroreflector 233 may be implemented as a component of the optical sensing unit. The retroreflector 233 can replace the opaque mask 219 illustrated in FIG. 2C and can be located between the center region 209 (including the first light emitters 206 and the second light emitters 208) and the peripheral region 205 (including the light detectors 204). The retroreflector 233 may be a ring or an arc that is located around the center region 209. Alternatively, the retroreflector 233 can be located in one or more sections of the ring, while an opaque mask (e.g., opaque mask 219) can be located in one or more other sections of the ring. In some examples, one or more sections of the ring may not include a retroreflector 233 or an opaque mask 219.

The retroreflector 233 can be a component capable of reflecting light back along a direction that is parallel or nearly parallel to, but opposite in direction from its origin, irrespective of the angle of incidence. For example, light from the light emitters 206 may reflect off an interface (e.g., the outer surface, which may be the surface opposite the retroreflector 233) of the window 203. The light may reach the light detector 204 without interacting with the sample, and thus may not include physiological information. Instead of allowing the light to reach the light detector 204, the retroreflector 233 may reflect the light back to the interface (e.g., in the direction away from the light detector 204).

In some examples, the retroreflector can include one or more features having properties (e.g., 20 degrees, 60 degrees, 90 degrees, etc.) configured to selectively reflect light within a range of angles of incidence. In some examples, the one or more features can reflect light back in the same direction that is not parallel or nearly parallel to the incident light. In some examples, the retroreflector 233 may be wavelength independent, where a wide range of wavelengths can be reflected back.

Figure 2F:
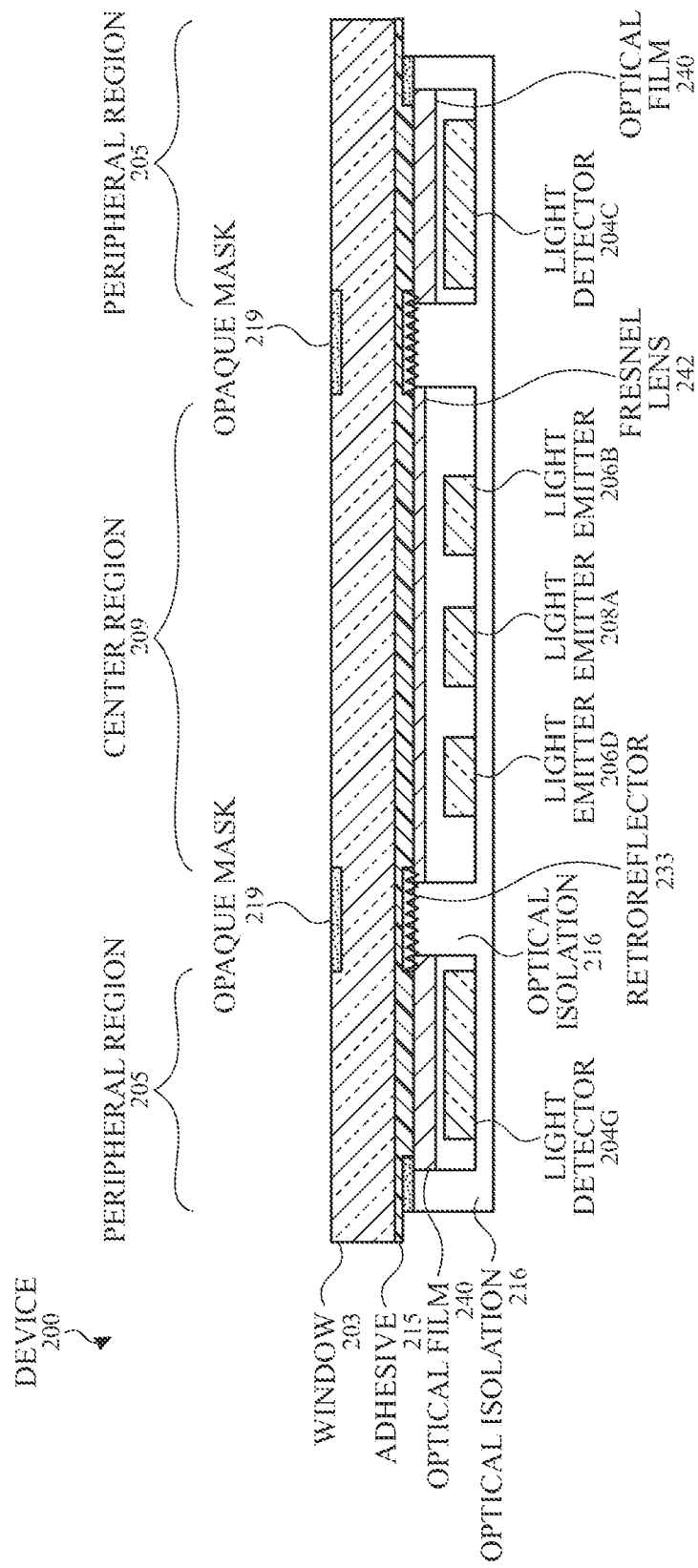
FIG. 2F illustrates a cross-sectional view of an exemplary electronic dev ice including a concentric architecture, a retroreflector, and an opaque mask according to examples of the disclosure.

In some instances, the device 200 can include both a retroreflector 233 and an opaque mask 219, as illustrated in FIG. 2F. The retroreflector 233 can be located closer to the light emitters 206 and 208 (and/or light detector 204C) than the opaque mask 219. The opaque mask 219 can further help to prevent unwanted light from reaching the light detector 204 by including a material that can absorb the light rays that reflect off the one or more interfaces of the window 203. In some examples, as illustrated in the FIGS. 2E-2F, the retroreflector 233 and/or the opaque mask 219 can have a larger width (e.g., can overhang) than the optical isolation 216, which can reduce the cross-talk between the light emitters 206 and 208 and the light detectors 204. In some examples, the opaque mask 219 can have a smaller width than the retroreflector 233. Additionally or alternatively, the retroreflector 233 and/or the opaque mask 219 can include one or more materials (e.g., black ink) that conceal underlying components (e.g., optical isolation 216) from the user's eyes.

Figure 2G:
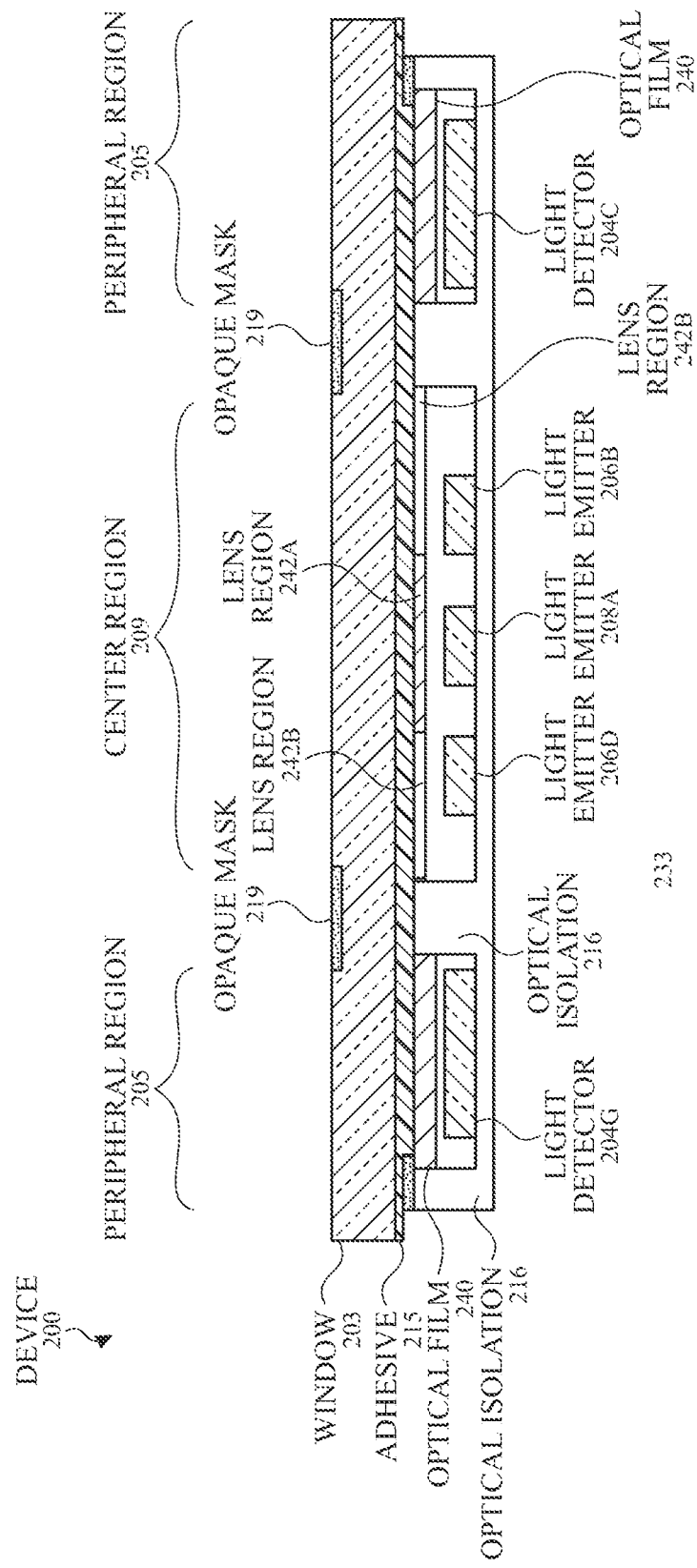
FIG. 2G-2H illustrate cross-sectional and top views, respectively, of an exemplary electronic device including a lens with multiple regions according to examples of the disclosure.
Figure 2H:
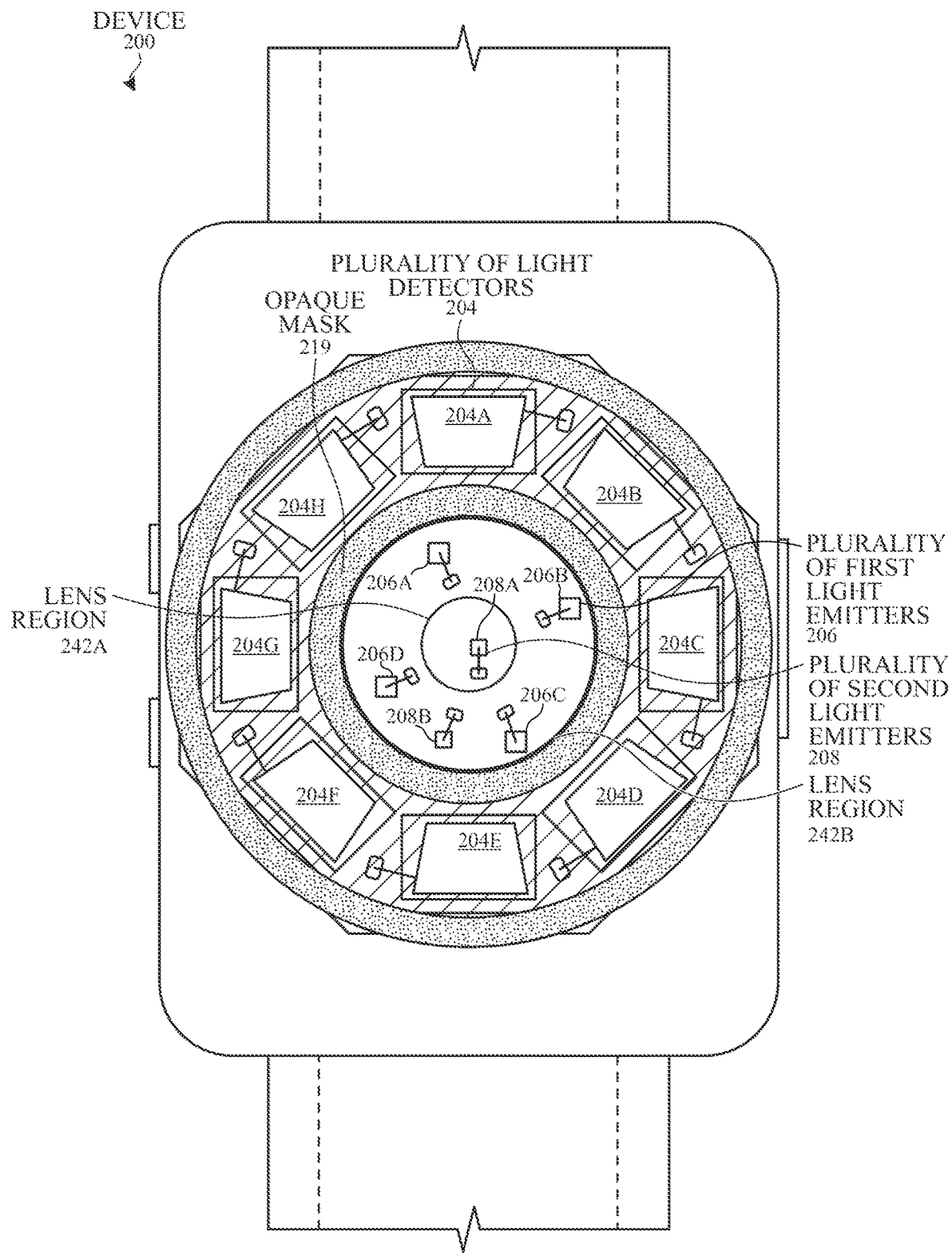

In some examples, the device 200 can include a lens having multiple regions. FIG. 2G-2H illustrate cross-sectional and top views, respectively, of an exemplary electronic device including a lens with multiple regions according to examples of the disclosure. The device 200 can include lens region 242A and lens regions 242B (collectively referred to as lens 242). The different lens regions can have different optical and/or physical properties. For example, the lens region 242A can be a Fresnel lens that overlays (i.e., located in the field of view of) the second light emitter 208A. The lens regions 242A can include a plurality of features (e.g., ridges) for focusing (e.g., collimating the light emitted by the second light emitter 208A. The lens regions 242B can overlay at least two of the plurality of first light emitters 206. The lens regions 242B can include one or more other features (e.g., prisms) for controlling the light emitted by the plurality of first light emitters 206.

In some instances, the lens 242 can be a layer separate from the windows 203. In other examples, the lens 242 can be formed as a part of (i.e., inseparable from) the windows 203.

In instances where the second light emitter(s) 208 emit a second light having a second wavelength, such as infrared light, and the first light emitters 206 emit a first light having a first wavelength, such as visible (e.g., green) light, the properties of the second light may differ from the first light. For example, the second light may have a lower signal intensities (or signal-to-noise ratio (SNR)), and the lens region 242A (associated with the second light) may have one or more properties for enhancing the relative signals or SNR.

Exemplary Operation of the Sensing Unit

Figure 3:
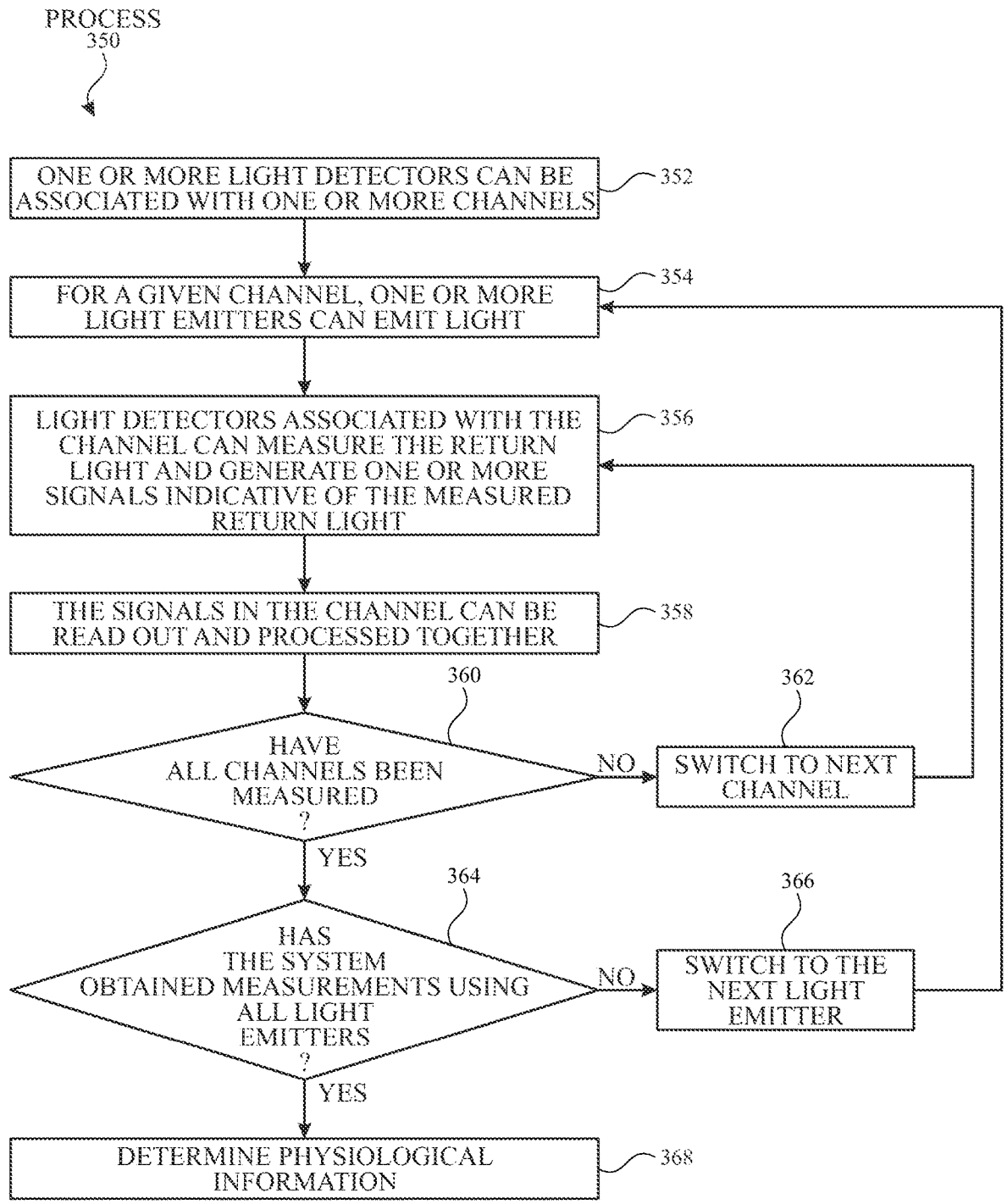
FIG. 3 illustrates an exemplary process flow using a binning technique for one or more channels according to examples of the disclosure.

The sensing unit can be operated using one or more binning techniques. FIG. 3 illustrates an exemplary process flow using a binning technique for one or more channels according to examples of the disclosure. One or more light detectors (e.g., all of the plurality of light detectors 204) can be associated with one or more channels (step 352 of process 350). In some examples, the channels can be dynamically changed based on the selected light emitter (step 353 of process 350). In some examples, the channels can be dynamically changed based on the spacing.

For a given channel, one or more light emitters (e.g., second light emitter 208A) can emit light (e.g., infrared light) (step 354 of process 350). A portion of the light can be absorbed by the user's skin, vasculature, and/or blood, and a portion of the light can return to the light detectors. The light detector(s) associated with the given channel can measure the return light and can generate one or more signals indicative of the measured return light (step 356 of process 350). The signals in the channel may be read out and processed (e g, summed) together, for example, to produce a channel signal (step 358 of process 350). The process can measure channels sequentially or concurrently. In the scenarios where the channels are measured sequentially, the process can be repeated for other channels until some or all channels are measured for a given light emitter. In some examples, multiple (including all) channels may be readout simultaneously, where signals within the same channel are processed separately from signals from other channels. Another light emitter (e.g., first light emitter 206A) can be selected for the measurements (step 364 and step 366 of process 350). Measuring multiple light emitters can allow the system to measure multiple regions of the user's skin for enhanced measurement accuracy. From the binned signals, the physiological information can be determined (step 368 of process 350).

Examples of the disclosure can include a single channel wherein some (including all) of the light detectors are associated with the single channel. With a single channel, all the signals from all of the plurality of light detectors can be processed together. The single channel association can allow higher total signal collection, which can increase the SNR for the light emitter 408A. Examples of the disclosure can further include each light detector associated with a unique channel. For example, the system can be configured with eight light detectors and eight channels. In this manner, the signal from each light detector can be processed separately.

Figure 4A:
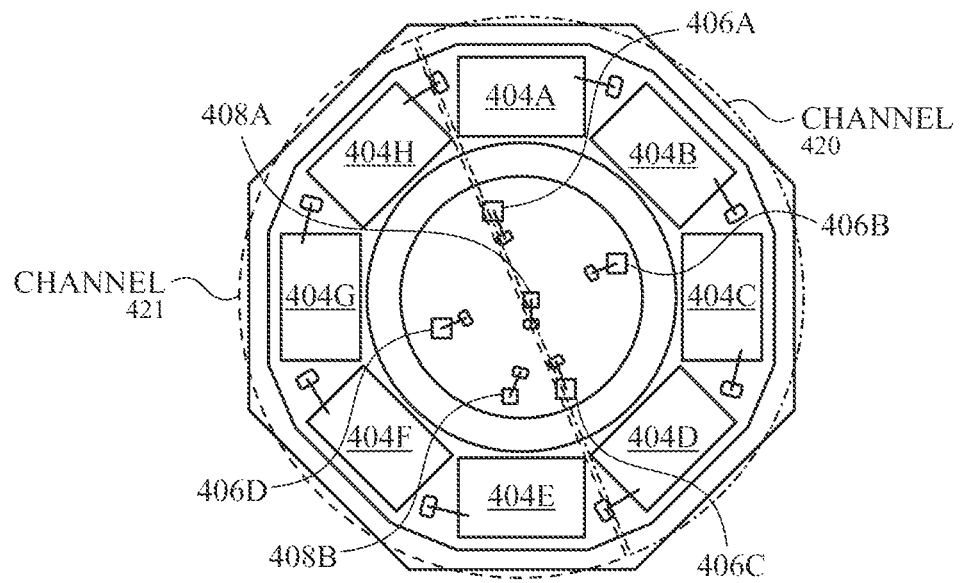
FIGS. 4A-4E illustrate exemplary associations of the light detectors to channels according to examples of the disclosure.

Additionally or alternatively, the system can be configured with other associations. FIGS. 4A-4E illustrate exemplary associations of the light detectors to channels according to examples of the disclosure. FIG. 4A illustrates two channels, where light detectors (e.g., light detector 404A, light detector 404B, light detector 404C, and light detector 404D) located on one side of the device can be associated with a first channel 420, and light detectors (e.g., light detector 404E, light detector 404F, light detector 404G, and light detector 404H) located on the other side of the device can be associated with a second channel 421. The unique relationships between each light emitter relative to the channels can lead to different information. Generally, the signal information may include a higher signal intensity for shorter separation distances between a light emitter and a light detector. When one light emitter is emitting light (i.e., activated), the signal information measured by each channel may be the same. For example, when light emitter 406A is emitting light, the light can be detected by all of the light detectors associated with a given channel. Channel 420 and channel 421 can include high signal information from light detector 404A and light detector 404H, respectively, along with low signal information from light detector 404D and light detector 404E, respectively. When another light emitter is emitting light, the signal information measured by each channel may differ. For example, when light emitter 406B is emitting light, channel 420 may include high signal information from light detector 404B and light detector 404C, along with moderate signal information from light detector 404A and light detector 404D. Channel 421 may include low signal information from light detector 404E, light detector 404H, light detector 404F, and light detector 404G. In this manner, the same light detectors can measure different sets of signals depending on which light emitter is activated.

Although the figure illustrates one channel as including the light detectors located on the right side and the other channel as including the light detectors located on the left side, examples of the disclosure can include the same number (e.g., two) of channels, but the associations including different light detectors. For example, the channel 420 can include the light detector 404C, the light detector 404D, the light detector 404E, and the light detector 404F, while the channel 421 can include the light detector 404G, the light detector 404H, the light detector 404A, and the light detector 404B (not shown). In some examples, the channel associations can be based on the relative location of the light emitter.

Figure 4B:
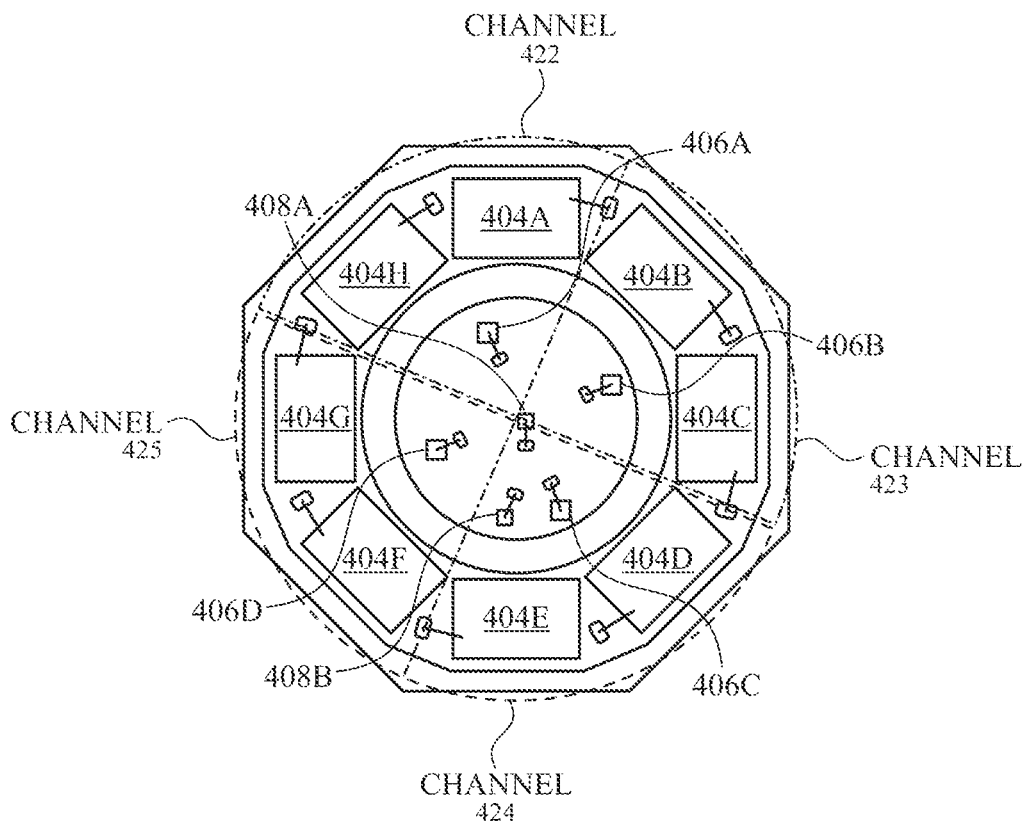

FIG. 4B illustrates four channels according to examples of the disclosure. Each channel can include two adjacent light detectors with an emitter having the same separation distance relative to the centers of the light detectors. For example, the channel 422 can include the light detector 404A and the light detector 404H; the channel 423 can include the light detector 404B and the light detector 404C; the channel 424 can include the light detector 404D and the light detector 404E; and the channel 425 can include the light detector 404F and the light detector 404G. The unique relationships between each light emitter relative to the channels can lead to different information. For example, the signal from the channel 422 can include different information then the channel 424 when the light emitter 406A is activated. With a higher number of channels (e.g., relative to the two channel association illustrated in FIG. 4A), localization of the measurement region on the user's skin can be enhanced, thereby increasing the SNR for the measurements. The localization of a measurement region can refer to the amount of information in the signal that is from the region proximate to a given light detector(s).

Figure 4C:
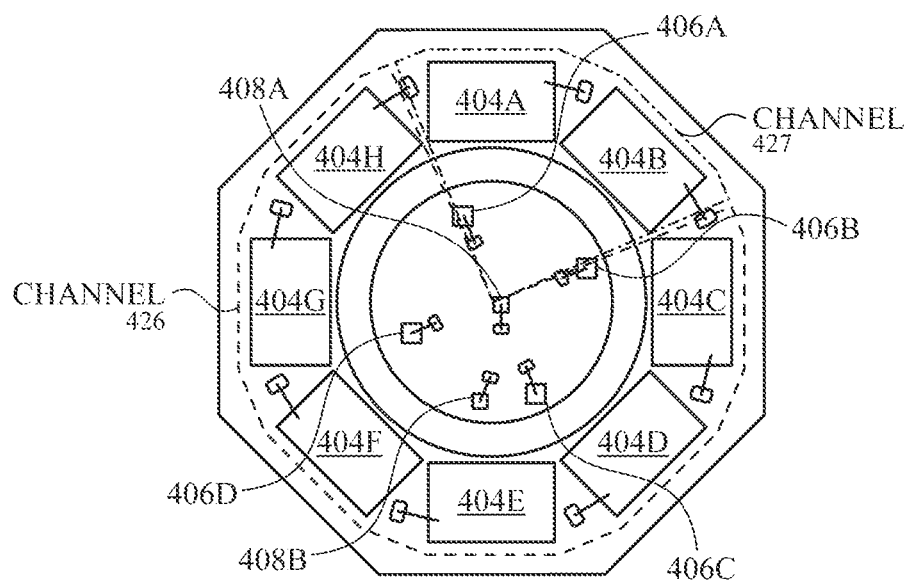

FIG. 4C illustrates two channels, wherein the channels may be non-uniformly allocated. In some instances, the number of light detectors associated with each channel can differ. For example, the channel 426 can include six light detectors (e.g., the light detector 404C, the light detector 404D, the light detector 404E, the light detector 404F, the light detector 404G, and the light detector 404H), and the channel 427 can include two light detectors (e.g., the light detector 404A and the light detector 404B). The system can be configured such that signals from one channel may be utilized for one type of information, and the signals from the other channel may be utilized for another type of information. For example, the channel 427 may have increased localization of a targeted measurement region on the user's skin and can be used for determining the user's physiological information. With decreased localization, channel 426 can be used for off-wrist detection and/or ambient light sensing. The signal from channel 426 can, for example, interrupt or be used for adjusting measurements associated with channel 427. As another example, channel 426 can have a larger sampling area than channel 427. The light detectors can be associated with a certain channel based on the signal quality.

Figure 4D:
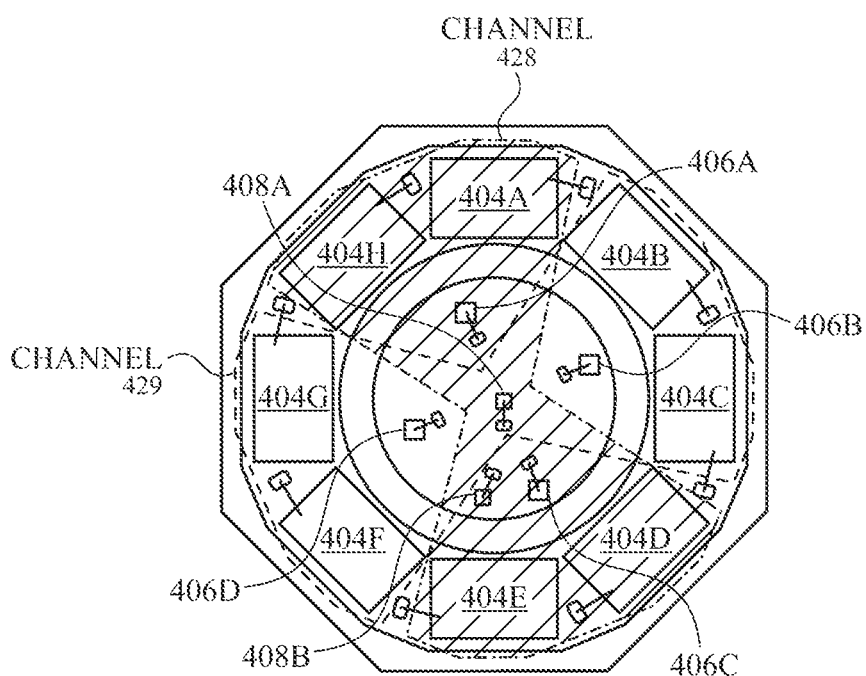

FIG. 4D illustrates multiple channels, where at least one channel includes non-neighboring light detectors according to examples of the disclosure. Channel 428 can include a first set of neighboring light detectors 404A and 404H and a second set of neighboring light detectors 404D and 404E, where the first set can be spatially separated (i.e., non-adjacent) along the concentric arrangement from the second set by at least one other (i.e., not included in the same channel) light detector. Channel 429 can include a first set of neighboring light detectors 404B and 404C and a second set of neighboring light detectors 404F and 404G, where the first set can be spatially separated from the second set by at least one other light detector. That is, one or more of the first and second channels can include two sets of adjacent light detectors (e.g., a first set can include light detector 404A and light detector 404H), where the two sets can be non-adjacent (e.g., a second set can include light detector 404D and light detector 404E, where the second set can non-adjacent to the first set). The first and second channels can have one or more different light detectors (e.g., light detector 404G may not be included in both first and second channels).

In this channel association, one set of light detectors can measure pulsatile information, while the other set of light detectors can measure non-pulsatile (e.g., dark) information. For example, when light emitter 406A is activated, pulsatile information for channel 428 can be generated by light detector 404A and light detector 404H, but may not be generated by light detector 404D and light detector 404E. Which light detector(s) measures pulsatile information for a given channel may depend on the activated light emitter. For example, pulsatile information for the channel 428 may not be measured by the light detector 404A and the light detector 404H when another light emitter (e.g., light emitter 406B) is activated; the another light emitter may be one that is not proximate to the respective light detector(s). Instead, the light detector 404D and the light detector 404E may generate pulsatile information when the light emitter 406B is activated.

In this manner, the same channel can effectively be used to measure different locations. For example, the light emitter 406A and the light emitter 406D can be assigned to the same channel 428. Signals measured by a first one or more light detectors 404 in the channel may measure useful information when one light emitter is active, while a second one or more light detectors 404 in the same channel may not. Subsequently, the detectors that measure useful information (e.g., included in the determination of physiological information) may differ when another light emitter is active.

Figure 4E:
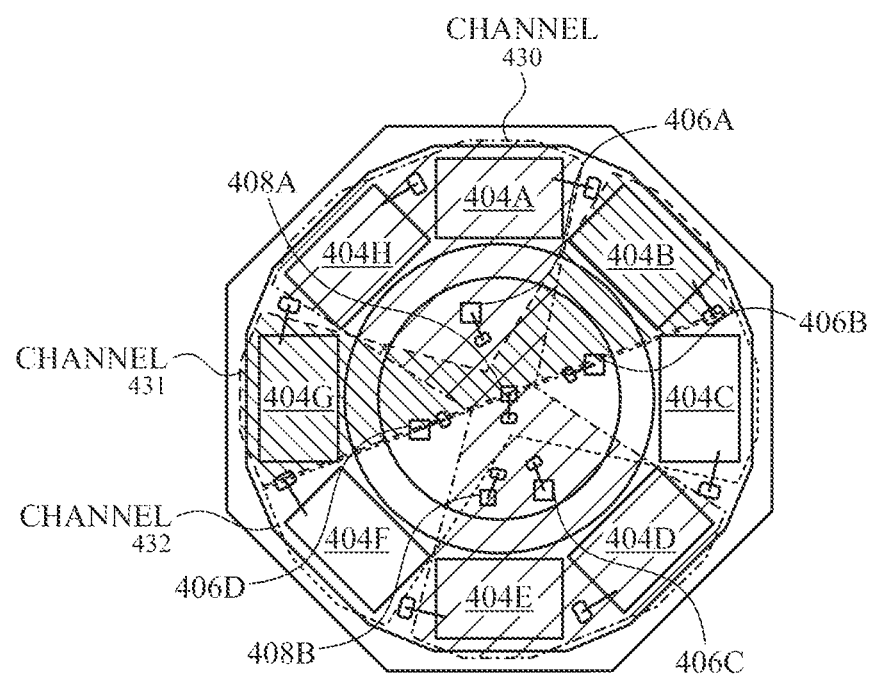

FIG. 4E illustrates three channels, where each channel may include different levels of signal information. The first association can include two sets of adjacent light detector, the two sets being non-adjacent (as discussed in the context of FIG. 4D), while the second association can include one or more light detectors adjacent to at least one light detector in the first association (e.g., light detector 404G can be adjacent to light detector 404H). For example, channel 430 can include the light detector 404A, the light detector 404H, the light detector 404D, and the light detector 404E. Channel 431 can include the light detector 404B and the light detector 404G; and channel 432 can include the light detector 404C and the light detector 404F. With light emitter 406A activated, the channel 430 may include the highest level of pulsatile signal information, channel 431 may include a moderate level, and channel 432 may include the lowest level. With light emitter 406B or light emitter 406D activated, the channel 431 and the channel 432 may include the highest level of pulsatile signal information, and the channel 430 may include the lowest level. With light emitter 406C activated, the channel 430 may include the highest level of pulsatile information, the channel 432 may include a moderate level, and the channel 431 may include the lowest level.

In some examples, the binning and channel associations may be dynamically changed without user interaction. The channel association can be based on the mode of operation. For example, when the system is in a first measurement operation mode, the system can be configured with a single channel including all eight light detectors. When the system switches to a second measurement operation mode, the system can dynamically switch to multiple (e.g., two, three, four, etc.) channels (e.g., as illustrated FIGS. 4A-4E).

In some examples, the system can switch to a certain channel association based on the measured signal information. For example, if the system is configured with two channels, as illustrated in FIG. 4A and the channel 420 generates higher pulsatile signal information after a certain number of measurements than the channel 421, the system may switch to the channel association shown in FIG. 4C. If, after the channel association switch, the higher pulsatile signal information is associated with the channel 427, the system may determine that one or more regions on the user's skin (e.g., localized in close proximity to the channel 427) may be most optimal for the given user. In this manner, the system can be tailored to the user, user conditions (e.g., one or more materials, such as the user's sleeve, inadvertently blocking optical components), and/or environmental conditions (e.g., higher levels of ambient light incident on one or more light detectors).

The above discussed channel associations can be implemented in post-processing where one or more (including all) of the light detectors can be hardwired together. Examples of the disclosure can further include one or more switches for dynamically switching which light detectors are electrically coupled (e.g., hardwired) together. Additionally or alternatively, one or more light detectors and/or channels may be deactivated. For example, if the system determines that the channel 427 (illustrated in FIG. 4C) includes the highest level of pulsatile information, the system may deactivate light detectors (e.g., light detector 404C, light detector 404D, light detector 404E, light detector 404F, light detector 404G, and light detector 404H) included in another channel, such as channel 426, to save power.

Figure 5:
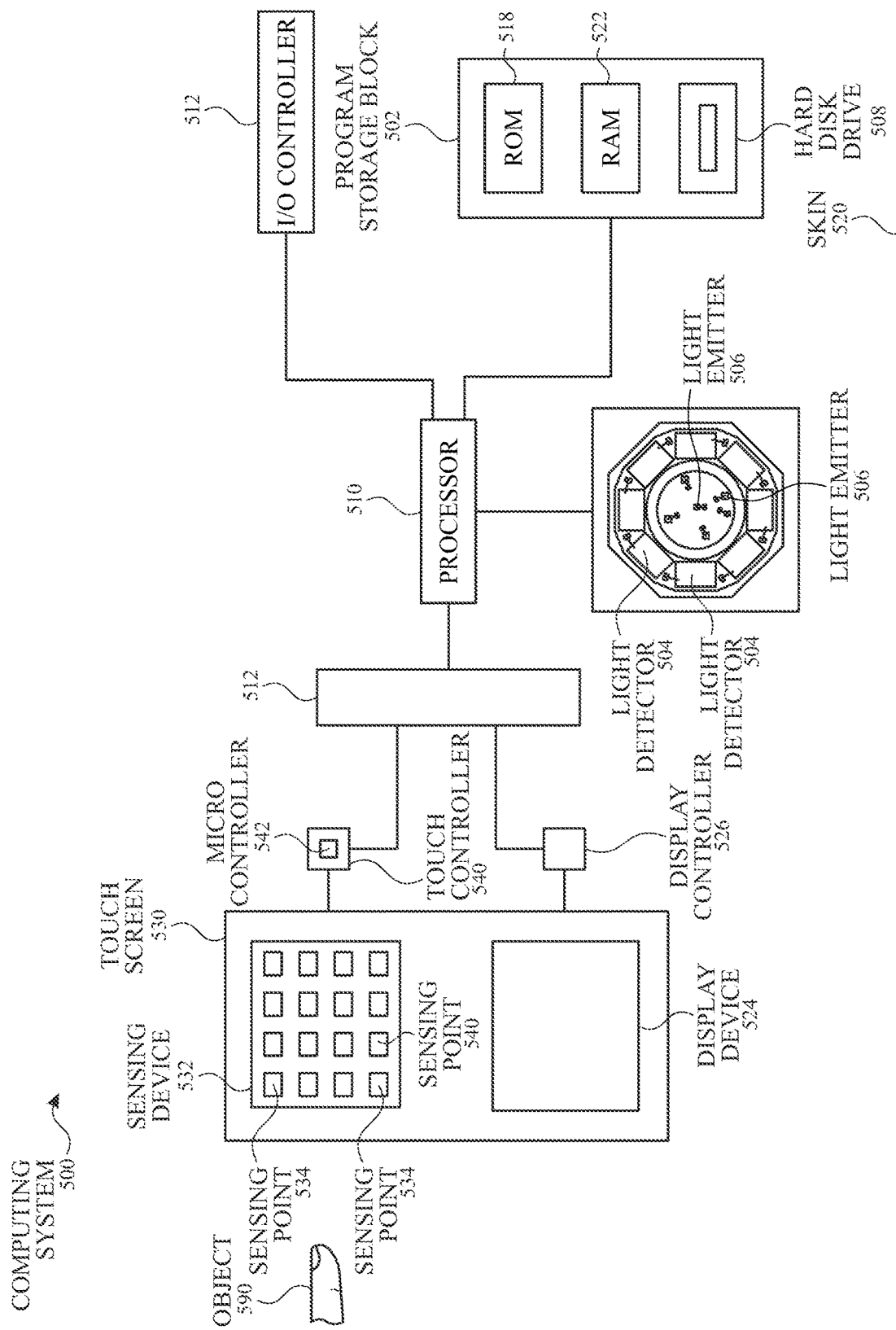
FIG. 5 illustrates an exemplary block diagram of a computing system comprising light emitters and light detectors for measuring a signal associated with a user's physiological state according to examples of the disclosure.

FIG. 5 illustrates an exemplary block diagram of a computing system comprising the concentric architecture for optical sensing according to examples of the disclosure. Computing system 500 can correspond to any of the computing devices illustrated in FIGS. 1A-1C. Computing system 500 can include a processor 510 configured to execute instructions and to carry out operations associated with computing system 500. For example, using instructions retrieved from memory, processor 510 can control the reception and manipulation of input and output data between components of computing system 500. Processor 510 can be a single-chip processor or can be implemented with multiple components.

In some examples, processor 510 together with an operating system can operate to execute computer code and produce and use data. The computer code and data can reside within a program storage block 502 that can be operatively coupled to processor 510. Program storage block 502 can generally provide a place to hold data that is being used by computing system 500. Program storage block 502 can be any non-transitory computer-readable storage medium (excluding signals), and can store, for example, history and/or pattern data relating to PPG signal and perfusion index values measured by one or more light detectors such as light detectors 504. By way of example, program storage block 502 can include Read-Only Memory (ROM) 518, Random-Access Memory (RAM) 522, hard disk drive 508 and/or the like. The computer code and data could also reside on a removable storage medium and loaded or installed onto the computing system 500 when needed. Removable storage mediums include, for example, CD-ROM, DVD-ROM, Universal Serial Bus (USB), Secure Digital (SD), Compact Flash (CF), Memory Stick, Multi-Media Card (MMC) and a network component.

Computing system 500 can also include an input/output (I/O) controller 512 that can be operatively coupled to processor 510, or it can be a separate component as shown. I/O controller 512 can be configured to control interactions with one or more I/O devices. I/O controller 512 can operate by exchanging data between processor 510 and the I/O devices that desire to communicate with processor 510. The I/O devices and I/O controller 512 can communicate through a data link. The data link can be a one-way link or a two-way link. In some cases, I/O devices can be connected to I/O controller 512 through wireless connections. By way of example, a data link can correspond to PS/2, USB, Firewire, IR, RF, Bluetooth or the like.

Computing system 500 can include a display device 524 that can be operatively coupled to processor 510. Display device 524 can be a separate component (peripheral device) or can be integrated with processor 510 and program storage block 502 to form a desktop computer (e.g., all-in-one machine), a laptop, handheld or tablet computing device of the like. Display device 524 can be configured to display a graphical user interface (GUI) including perhaps a pointer or cursor as well as other information to the user. By way of example, display device 524 can be any type of display including a liquid crystal display (LCD), an electroluminescent display (ELD), a field emission display (FED), a light emitting diode display (LED), an organic light emitting diode display (OLED) or the like.

Display device 524 can be coupled to display controller 526 that can be coupled to processor 510. Processor 510 can send raw data to display controller 526, and display controller 526 can send signals to display device 524. Data can include voltage levels for a plurality of pixels in display device 524 to project an image. In some examples, processor 510 can be configured to process the raw data.

Computing system 500 can also include a touch screen 530 that can be operatively coupled to processor 510. Touch screen 530 can be a combination of sensing device 532 and display device 524, where the sensing device 532 can be a transparent panel that is positioned in front of display device 524 or integrated with display device 524. In some cases, touch screen 530 can recognize touches and the position and magnitude of touches on its surface. Touch screen 530 can report the touches to processor 510, and processor 510 can interpret the touches in accordance with its programming. For example, processor 510 can perform tap and event gesture parsing and can initiate a wake of the device or powering on one or more components in accordance with a particular touch.

Touch screen 530 can be coupled to a touch controller 540 that can acquire data from touch screen 530 and can supply the acquired data to processor 510. In some cases, touch controller 540 can be configured to send raw data to processor 510, and processor 510 can process the raw data. For example, processor 510 can receive data from touch controller 540 and can determine how to interpret the data. The data can include the coordinates of a touch as well as pressure exerted. In some examples, touch controller 540 can be configured to process raw data itself. That is, touch controller 540 can read signals from sensing points 534 located on sensing device 532 and can turn the signals into data that the processor 510 can understand.

Touch controller 540 can include one or more microcontrollers such as microcontroller 542, each of which can monitor one or more sensing points 534. Microcontroller 542 can, for example, correspond to an application specific integrated circuit (ASIC), which works with firmware to monitor the signals from sensing device 532, process the monitored signals, and report this information to processor 510.

One or both display controller 526 and touch controller 540 can perform filtering and/or conversion processes. Filtering processes can be implemented to reduce a busy data stream to prevent processor 510 from being overloaded with redundant or non-essential data. The conversion processes can be implemented to adjust the raw data before sending or reporting them to processor 510.

In some examples, sensing device 532 can be based on capacitance. When two electrically conductive members come close to one another without actually touching, their electric fields can interact to form a capacitance. The first electrically conductive member can be one or more of the sensing points 534, and the second electrically conductive member can be an object 590 such as a finger. As object 590 approaches the surface of touch screen 530, a capacitance can form between object 590 and one or more sensing points 534 in close proximity to object 590. By detecting changes in capacitance at each of the sensing points 534 and noting the position of sensing points 534, touch controller 540 can recognize multiple objects, and determine the location, pressure, direction, speed, and acceleration of object 590 as it moves across the touch screen 530. For example, touch controller 540 can determine whether the sensed touch is a finger, tap, or an object covering the surface.

Sensing device 532 can be based on self-capacitance or mutual capacitance. In self-capacitance, each of the sensing points 534 can be provided by an individually charged electrode. As object 590 approaches the surface of the touch screen 530, the object can capacitively couple to those electrodes in close proximity to object 590, thereby stealing charge away from the electrodes. The amount of charge in each of the electrodes can be measured by the touch controller 540 to determine the position of one or more objects when they touch or hover over the touch screen 530. In mutual capacitance, sensing device 532 can include a two layer grid of spatially separated lines or wires (not shown), although other configurations are possible. The upper layer can include lines in rows, while the lower layer can include lines in columns (e.g., orthogonal). Sensing points 534 can be provided at the intersections of the rows and columns. During operation, the rows can be charged, and the charge can capacitively couple from the rows to the columns. As object 590 approaches the surface of the touch screen 530, object 590 can capacitively couple to the rows in close proximity to object 590, thereby reducing the charge coupling between the rows and columns. The amount of charge in each of the columns can be measured by touch controller 540 to determine the position of multiple objects when they touch the touch screen 530.

Computing system 500 can also include one or more light emitters such as light emitters 506 and one or more light detectors such as light detectors 504 proximate to skin 520 of a user. Light emitters 506 can be configured to generate light, and light detectors 504 can be configured to measure the return. Light detectors 504 can send measured raw data to processor 510, and processor 510 can perform noise and/or artifact cancelation to determine the PPG signal and/or perfusion index. Processor 510 can dynamically activate light emitters and/or light detectors based on an application, user skin type, and usage conditions. In some examples, some light emitters and/or light detectors can be activated, while other light emitters and/or light detectors can be deactivated to conserve power, for example. In some examples, processor 510 can store the raw data and/or processed information in a ROM 518 or RAM 522 for historical tracking or for future diagnostic purposes.

Figure 6:
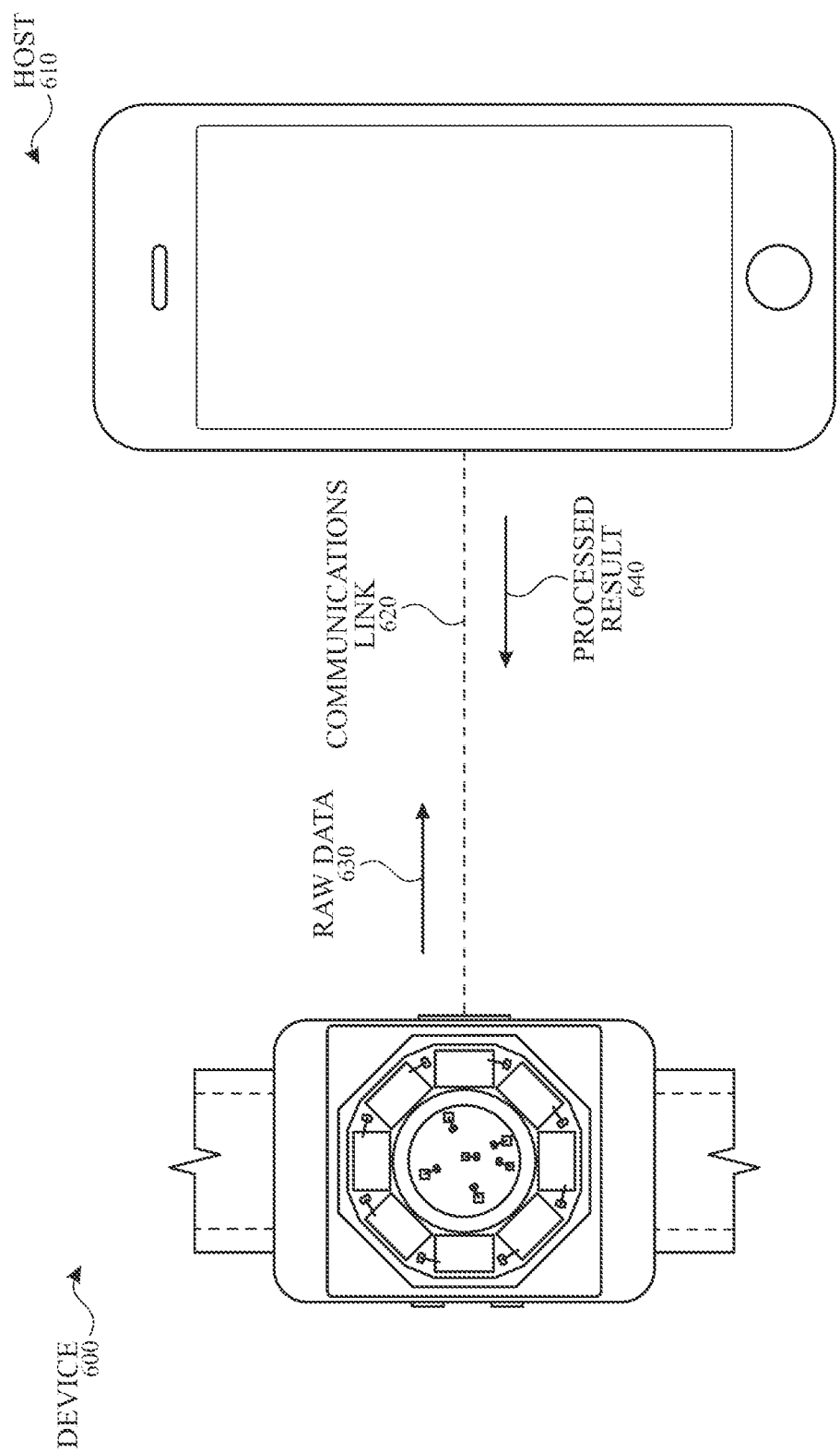
FIG. 6 illustrates an exemplary configuration in which an electronic device is connected to a host according to examples of the disclosure.

In some examples, the light detectors can measure light information and a processor can determine a PPG signal and/or perfusion index from the return light. Processing of the light information can be performed on the device as well. In some examples, processing of light information need not be performed on the device itself. FIG. 6 illustrates an exemplary configuration in which an electronic device is connected to a host according to examples of the disclosure. Host 610 can be any device external to device 600 including, but not limited to, any of the systems illustrated in FIGS. 1A-1C or a server. Device 600 can be connected to host 610 through communications link 620. Communications link 620 can be any connection including, but not limited to, a wireless connection and a wired connection. Exemplary wireless connections include Wi-Fi, Bluetooth, Wireless Direct and Infrared. Exemplary wired connections include Universal Serial Bus (USB), FireWire, Thunderbolt, or any connection requiring a physical cable.

In operation, instead of processing light information from the light detectors on the device 600 itself, device 600 can send raw data 630 measured from the light detectors over communications link 620 to host 610. Host 610 can receive raw data 630, and host 610 can process the light information. Processing the light information can include canceling or reducing any noise due to artifacts and determining physiological signals such as a user's heart rate. Host 610 can include algorithms or calibration procedures to account for differences in a user's characteristics affecting PPG signal and perfusion index. Additionally, host 610 can include storage or memory for tracking a PPG signal and perfusion index history for diagnostic purposes. Host 610 can send the processed result 640 or related information back to device 600. Based on the processed result 640, device 600 can notify the user or adjust its operation accordingly. By offloading the processing and/or storage of the light information, device 600 can conserve space and power-enabling device 600 to remain small and portable, as space that could otherwise be required for processing logic can be freed up on the device.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate may allow a user to track or otherwise gain insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

A device is disclosed. In some examples, the device comprises: an optical sensing unit comprising: a center region including: a plurality of first light emitters configured to emit first light paths having first wavelengths; one or more second light emitters configured to emit second light paths having second wavelengths, different from the first wavelengths, wherein the plurality of first light emitters is located closer to a peripheral region than the one or more second light emitters; and the peripheral region located around the center region, the peripheral region including: a plurality of light detectors configured to detect the first light paths and the second light paths, wherein the plurality of light detectors is oriented in a concentric arrangement. Additionally or alternatively, the device comprises: a lens including a plurality of regions, the plurality of regions including: a first region overlaying the plurality of first light emitters; and a second region overlaying the one or more second light emitters, wherein optical properties of the first region differ from optical properties of the second region. Additionally or alternatively, in some examples, a center of each light detector is located a first separation distance away from at least one of the one or more second light emitters. Additionally or alternatively, in some examples, each light detector is located a first separation distance from one of the one or more second light emitters and a second separation distance from one of the plurality of first light emitters, wherein the first separation distance is greater than the second separation distance. Additionally or alternatively, in some examples, another light detector is located a third separation distance from the one of the plurality of first light emitters, wherein the third separation distance is greater than the first separation distance, the second separation distance, or both. Additionally or alternatively, in some examples, each of the plurality of first light emitters is located at a radial angle relative to a center of the center region, and edges of two of the plurality of light detectors are located at the radial angle relative to the center of the center region. Additionally or alternatively, in some examples, each of the first light emitters is located such that a separation distance between the respective first light emitter and one of the plurality of light detectors is the same as the separation distance between the respective first light emitter and others of the plurality of light detectors, wherein the one of the plurality of light detectors and the other of the plurality of light detectors are adjacent light detectors. Additionally or alternatively, in some examples, the device further comprises: an optical isolation located between the plurality of first and second light emitters and the plurality of light detectors. Additionally or alternatively, the optical isolation is ring-shaped. Additionally or alternatively, in some examples, walls of the optical isolation define one or more cavities, wherein the plurality of first light emitters and the one or more second light emitters are located in a cavity separate from the plurality of light detectors. Additionally or alternatively, in some examples, the device further comprises: a retroreflector located between the center region and the peripheral region, wherein the retroreflector is configured to reflect light in a direction away from at least one of the plurality of detectors. Additionally or alternatively, in some examples, the device further comprises: one or more windows located proximate to the center region and the peripheral region; and an opaque mask located between the center region and the peripheral region, wherein the opaque mask is configured to absorb light reflecting off an interface of the one or more windows. Additionally or alternatively, in some examples, the device further comprises: a selective transparent layer located in the peripheral region, the selective transparent layer including a plurality of first sections and a plurality of second sections, wherein the plurality of first sections overlays one or more first portions of the peripheral region and the plurality of second sections overlays one or more second portions of the peripheral region, the one or more second portions overlay the plurality of light detectors. Additionally or alternatively, in some examples, the plurality of first sections includes material that is partially transparent to the first wavelengths and transparent to the second wavelengths. Additionally or alternatively, in some examples, the plurality of second sections excludes material. Additionally or alternatively, in some examples, the selective transparent layer is ring-shaped. Additionally or alternatively, in some examples, the device further comprises: a Fresnel lens located in the center region overlaying the plurality of first light emitters and the one or more second light emitters; and one or more optical film sections located in the peripheral region overlaying the plurality of light detectors, wherein the one or more optical film sections are configured to restrict light passing through the peripheral region. Additionally or alternatively, in some examples, the first wavelengths include one or more visible wavelengths, and the second wavelengths include one or more infrared wavelengths. Additionally or alternatively, in some examples, the first region of the lens is a Fresnel lens, and the second region of the lens includes a plurality of prisms.

A method for operating a device is disclosed. The method comprises: associating a plurality of light detectors to a plurality of channels during a first time; for each light emitter: emitting light from the respective light emitter; measuring at least a portion of the emitted light by the one or more channels; and selecting and changing to another association such that at least one of the plurality of light detectors is associated with a different channel during a second time, the selected another association based on one or more of the measurements. Additionally or alternatively, in some examples, the association during the first time or the second time includes each channel having adjacent light detectors. Additionally or alternatively, in some examples, the association during the first time or the second time includes each channel having a first set of one or more of the plurality of light detectors and a second set of one or more of the plurality of light detectors, the first set spatially separated from the second set. Additionally or alternatively, in some examples, the method further comprises: determining a physiological information using the measurement from the first set when one light emitter is emitting and using the measurement from the second set when another light emitter is emitting. Additionally or alternatively, in some examples, one association includes a single channel including all of the plurality of light detectors and another association includes multiple channels. Additionally or alternatively, in some examples, signals from the one association are used for primary measurement information, and signals from the other association are used for secondary measurement information. Additionally or alternatively, in some examples, the association during the first time includes two sets of adjacent light detectors, the two sets being non-adjacent. Additionally or alternatively, in some examples, at least one of the plurality of light detectors included in one of the plurality of channels during the first time is included in the same one of the plurality of channels during the second time.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

We claim:

1. A wearable electronic device comprising:
a device housing;
a strap attached to the device housing and configured to retain the device housing on a user's wrist;
a processor positioned within the device housing; and
an optical sensing unit positioned at least partially within the device housing and comprising:
a central region;
a peripheral region surrounding the central region;
a first light emitter positioned in the central region and configured to emit first light in a first wavelength range;
a second light emitter positioned in the central region and configured to emit second light in a second wavelength range that is different from the first wavelength range;
a set of light detectors positioned in the peripheral region and configured to detect the first light and the second light, the set of light detectors at least partially surrounding the first light emitter and the second light emitter; and
a selective transparent layer positioned in the peripheral region and comprising:
a first section positioned over a light detector of the set of light detectors and transparent to the second wavelength range; and
a second section surrounding the first section, the second section at least partially transparent to the first wavelength range and opaque to the second wavelength range.

2. The wearable electronic device of claim 1, wherein:
the first section of the selective transparent layer is one of a set of first sections;
each of the set of first sections is positioned over a respective light detector of the set of light detectors; and
the second section surrounds each of the set of first sections.

3. The wearable electronic device of claim 1, wherein:
the first wavelength range comprises infrared wavelengths; and
the second wavelength range comprises visible light wavelengths.

4. The wearable electronic device of claim 1, wherein:
the first section is at least partially transparent to the first wavelength range; and
the second section is fully transparent to the first wavelength range.

5. The wearable electronic device of claim 1, wherein the first section is an open portion of the selective transparent layer.

6. The wearable electronic device of claim 1, wherein:
the wearable electronic device further comprises a window positioned over the central region and the peripheral region of the optical sensing unit, the window defining a portion of an exterior surface of the wearable electronic device; and
the selective transparent layer is positioned along an interior surface of the window opposite the exterior surface.

7. The wearable electronic device of claim 1, wherein:
the optical sensing unit further comprises:
a first wall that extends around the central region between the central region and the peripheral region; and
a second wall that extends around the peripheral region;
the first light emitter and the second light emitter are positioned in a first cavity at least partially defined by the first wall; and
the set of light detectors is positioned in a second cavity that is at least partially defined by the first wall and the second wall and that extends around the first cavity.

8. The wearable electronic device of claim 7, wherein:
the optical sensing unit further comprises an optical isolation configured to at least partially enclose the first light emitter, the second light emitter, and the set of light detectors; and
the first wall, the second wall, the first cavity, and the second cavity cooperatively form the optical isolation.

9. The wearable electronic device of claim 7, wherein:
the wearable electronic device further comprises a window positioned over the central region and the peripheral region of the optical sensing unit, the window defining a portion of an exterior surface of the wearable electronic device; and
the optical sensing unit further comprises:
a lens positioned between the first cavity and the window;

an optical film positioned between the second cavity and the window;
a first opaque mask positioned between the first wall and the window and extending around the central region; and
a second opaque mask positioned between the second wall and the window.

10. A wearable electronic device, comprising:
a device housing defining an opening;
a processor positioned within the device housing;
a window positioned over the opening and defining a portion of an exterior surface of the wearable electronic device;
an optical sensing unit positioned beneath the window and comprising:
a central region;
a first light emitter positioned in the central region and configured to emit first light in a first wavelength range;
a set of second light emitters arranged around the first light emitter and configured to emit second light in a second wavelength range that is different from the first wavelength range;
a set of light detectors arranged around the set of second light emitters and configured to detect the first light and the second light; and
a selective transparent layer positioned between the set of light detectors and the window and comprising:
a set of first sections, each of the set of first sections positioned over a respective light detector of the set of light detectors and at least partially transparent to the second wavelength range; and
a second section surrounding each of the set of first sections, the second section transparent to the first wavelength range and at least partially non-transparent to the second wavelength range.

11. The wearable electronic device of claim 10, wherein the optical sensing unit further comprises a wall positioned between the set of second light emitters and the set of light detectors and extending around the first light emitter and the set of second light emitters.

12. The wearable electronic device of claim 11, wherein:
the optical sensing unit further comprises a lens positioned between the window and the first light emitter and the set of second light emitters; and
the wall extends around the lens.

13. The wearable electronic device of claim 11, wherein the optical sensing unit further comprises an opaque mask positioned between the wall and the window.

14. The wearable electronic device of claim 13, wherein:
the wall is a first wall;
the opaque mask is a first opaque mask; and
the optical sensing unit further comprises:
a second wall extending around the set of light detectors; and
a second opaque mask positioned between the second wall and the window.

15. The wearable electronic device of claim 11, wherein:
the wall is a first wall; and
the optical sensing unit further comprises:
a second wall extending around the set of light detectors; and
an optical film positioned between the set of light detectors and the window and between the first wall and the second wall.

16. The wearable electronic device of claim 10, wherein:
the first wavelength range comprises infrared wavelengths; and
the second wavelength range comprises visible light wavelengths.

17. An optical sensing unit for a wearable electronic device comprising:
an optical isolation comprising:
a first wall extending around and at least partially defining a first cavity;
a second wall extending around the first wall and at least partially defining a second cavity between the first wall and the second wall;
a first light emitter positioned in the first cavity and configured to emit first light in a first wavelength range;
a second light emitter positioned in the first cavity and configured to emit second light in a second wavelength range different from the first wavelength range;
a set of light detectors positioned in the second cavity of the optical sensing unit and configured to detect the first light and the second light; and
a selective transparent layer positioned over the second cavity and comprising:
a first section that is transparent to the second wavelength range; and
a second section surrounding the first section, the second section at least partially transparent to the first wavelength range and opaque to the second wavelength range, the second section configured to transmit light from the first wavelength range to the set of light detectors.

18. The optical sensing unit of claim 17, further comprising:
a Fresnel lens positioned over the first light emitter; and
a prism positioned over the second light emitter.

19. The optical sensing unit of claim 17, wherein:
the second light emitter is one of a set of second light emitters; and
the set of second light emitters is arranged around the first light emitter.

20. The optical sensing unit of claim 19, wherein:
the optical sensing unit further comprises:
a first lens region positioned over the first light emitter and comprising a Fresnel lens; and
a second lens region positioned over the set of second light emitters and comprising a set of prisms, each prism of the set of prisms positioned over a respective second light emitter of the set of second light emitters.

* * * * *